United States Patent
Weiner et al.

(10) Patent No.: US 10,420,547 B2
(45) Date of Patent: Sep. 24, 2019

(54) STAPLES AND STAPLE DELIVERY AND DRILL GUIDES

(71) Applicant: NEXTREMITY SOLUTIONS, INC., Warsaw, IN (US)

(72) Inventors: Lon S. Weiner, Rumson, NJ (US); Jorge Montoya, Berkley Heights, NJ (US); John R. Pepper, Cheshire, CT (US); Stuart D. Katchis, Scarsdale, NY (US); Lawrence Kiefer, Newark, NJ (US)

(73) Assignee: Nextremity Solutions, Inc., Warsaw, IN (US)

( * ) Notice: Subject to any disclaimer, the term of this patent is extended or adjusted under 35 U.S.C. 154(b) by 159 days.

(21) Appl. No.: 15/357,323

(22) Filed: Nov. 21, 2016

(65) Prior Publication Data

US 2017/0065276 A1    Mar. 9, 2017

Related U.S. Application Data

(63) Continuation of application No. PCT/US2015/031990, filed on May 21, 2015.
(Continued)

(51) Int. Cl.
  *A61B 17/064*  (2006.01)
  *A61B 17/068*  (2006.01)
  *A61B 17/17*   (2006.01)

(52) U.S. Cl.
  CPC ...... *A61B 17/0644* (2013.01); *A61B 17/0642* (2013.01); *A61B 17/0682* (2013.01); *A61B 17/17* (2013.01)

(58) Field of Classification Search
  CPC ............ A61B 17/0642; A61B 17/0644; A61B 17/0682; A61B 17/17; A61B 2017/0645; A61B 17/064; A61B 17/068; A61B 17/66
  See application file for complete search history.

(56) References Cited

U.S. PATENT DOCUMENTS 4,838,254 A * 6/1989 Gauthier ............ A61B 17/0642
                                                        606/75
4,887,601 A   12/1989 Richards
(Continued)

FOREIGN PATENT DOCUMENTS

FR    2 902 636 A1    12/2007

OTHER PUBLICATIONS

International Search Report and Written Opinion of the International Searching Authority issued for PCT Application PCT/US2015/031990 dated Aug. 21, 2015.
(Continued)

*Primary Examiner* — George J Ulsh
(74) *Attorney, Agent, or Firm* — Heslin Rothenberg Farley & Mesiti P.C.; Victor A. Cardona, Esq.

(57) ABSTRACT

The present disclosure provides staples, and corresponding staple guides, for applying a compressive force between biological elements. The staples may include a bridge portion and a pair of tines extending from the bridge portion configured for implantation into biological elements. The tines may be spaced a first distance in a first state of the bridge portion. The bridge portion may be elastically deformable into a second state with the pair of tines spaced a second distance that is greater than the first distance and the tines pre-loaded to apply a compressive force therebetween. The guides may include a staple engagement portion operable to maintain the biased state of the staple, and/or a drill guide portion operable to facilitate the formation of apertures spaced the second distance in the biological elements.

10 Claims, 24 Drawing Sheets

Related U.S. Application Data

(60) Provisional application No. 62/041,350, filed on Aug. 25, 2014, provisional application No. 62/001,261, filed on May 21, 2014.

(56) References Cited

U.S. PATENT DOCUMENTS

| | | |
|---|---|---|
| 9,017,331 B2 * | 4/2015 | Fox .................... A61B 17/0642 606/75 |
| 2004/0138705 A1 | 7/2004 | Heino |
| 2010/0036430 A1 | 2/2010 | Hartdegen et al. |
| 2014/0018809 A1 | 1/2014 | Allen |

OTHER PUBLICATIONS

International Preliminary Report on Patentability issued in International Application No. PCT/US2015/031990 dated Nov. 22, 2016.

* cited by examiner

STAPLES AND STAPLE DELIVERY AND DRILL GUIDES

CROSS-REFERENCE TO RELATED APPLICATIONS

This application is continuation of PCT Application PCT/US2015/031990 filed on May 21, 2015, entitled, Staples and Staple Delivery and Drill Guides, which claims priority to U.S. Provisional Patent Application No. 62/001,261 filed on May 21, 2014, entitled Tissue Staples and Staple Delivery and Drill Guides, and U.S. Provisional Patent Application No. 62/041,350 filed on Aug. 25, 2014, entitled Staples and Staple Delivery and Drill Guides, the entirety of which are hereby expressly incorporated by reference in their entireties.

BACKGROUND

The present disclosure generally relates to staples or retainers, and particularly relates to staples or retainers and staple or retainer delivery and drill guides.

Some staples are used in place of, or in addition to, sutures to hold biological elements together. For example, staples are commonly used to close openings, incisions, or wounds. Staples are also typically used to attach or couple biological elements together, such as bone segments. Stapling is relatively faster than suturing by hand, and also typically more accurate and consistent. As staples may be more consistent than sutures, they may be less likely to leak blood, air or other biological contents, and allow the ingress of foreign bodies.

Some biological elements may heal or form a single construct quicker and/or more securely when a compressive pressure or force is applied between the biological elements. For example, bone segments may fuse together quicker and more securely when a compressive force is applied and maintained across the junction between the bone segments. Further, when a compressive pressure or force is applied between biological elements, the biological elements may be less painful and more stable during a healing process of the biological elements.

As a result, improved staples that are able to apply a compressive pressure or force between biological elements are needed. Further, corresponding apparatus and systems are needed to quickly and accurately implement such improved staples.

SUMMARY OF THE INVENTION

In one aspect, the present disclosure provides a staple for applying a compressive force between biological elements. The staple includes a non-linearly extending bridge portion and a pair of tines. The pair of tines extend from the bridge portion and include free ends configured to be implanted into the biological elements. The pair of tines being spaced apart a first distance in a first state of the bridge portion. The bridge portion is elastically deformable into a second state such the pair of tines are spaced apart a second distance that is greater than the first distance.

In some embodiments, the pair of tines may extend from opposing ends of the bridge portion. In some embodiments, the bridge portion may extend between the pair of tines. In some such embodiments, the bridge portion may include a plurality of linearly extending portions that are angled with respect to each other. In some other such embodiments, the bridge portion may define an arcuate shape. In some other such embodiments, the bridge portion may define a serpentine pattern extending between the pair of tines. In some embodiments, in the second state of the bridge, the pair of tines may be pre-loaded to apply a compressive force between the tines.

In some embodiments, the bridge portion may include at least two distinct portions that extend at least partially between the pair of tines. In some embodiments, the at least two distinct portions of the bridge portion may extend along differing non-linear paths between the pair of tines. In some embodiments, at least one of the bridge portion and the pair of tines may have a circular or rectangular cross-section. In some embodiments, the bridge portion may have a cross-section that is larger proximate to the pair of tines than distal to tines. In some embodiments, the bridge portion may include an aperture.

In some embodiments, the bridge portion may extend between the pair of tines on a first side of the pair of tines. In some such embodiments, an intermediate portion of the bridge portion may be positioned furthest from of the pair of tines on the first side. In some embodiments, the bridge portion may extend between the pair of tines on a first side of the pair of tines and a second side of the pair of tines that substantially opposes the first side.

In some embodiments, each tine may extend along a first direction defined between the bridge portion and the free end thereof, and the bridge may portion extend between the tines along a second direction. In some such embodiments, an intermediate portion of the bridge portion between the pair of tines may be positioned further along the second direction toward the free end of the tines. In some other embodiments, the first and second directions may be substantially perpendicular. In some embodiments, each of the tines may include an engagement mechanism positioned on a portion of the tines that substantially faces the other tine of the pair of tines along the first direction. In such some embodiments, the engagement mechanisms of the pairs of tines include at least one barb structure.

In some embodiments, each engagement mechanism of the pairs of tines may include a first portion proximate to the free end of the respect tine and extending toward the bridge portion; a first ramp portion extending from the first portion toward the bridge portion and along the first direction toward the other tine of the pair of tines; a plateau portion extending from the first ramp portion toward the bridge portion; a second ramp portion extending from the plateau portion toward the bridge portion and along the first direction toward the other tine of the pair of tines a distance greater than the first ramp portion; and a relief portion extending from the plateau portion and at least along the first direction away from the other tine of the pair of tine, the intersection of the relief portion and the second ramp portion forming a tip. In some such embodiments, the second ramp portion and the relief portion may form a barb structure. In some other such embodiments, each engagement mechanism of the pairs of tines may further include a plurality of the barb structures. In some other such embodiments, the first portion of the engagement mechanism may include a first portion proximate to the free end of the respect tine that extends toward the bridge portion and along the first direction toward the other tine of the pair of tines, and a second portion that extends from the first portion to the first ramp portion and along the first direction away from the other tine of the pair of tines.

In another aspect, the present disclosure provides a method of compressing two biological elements. The method includes obtaining a staple that includes a bridge portion extending non-linearly between a pair of tines, the tines being spaced a first distance in a first state of the bridge portion. The method also includes forming a first pair of apertures within a pair of biological elements, the first pair of apertures being spaced a second distance that is greater than the first distance. The method further includes elastically deforming the bridge portion of the staple into a second state to increase the space between of the first pair of tines from the first distance to the second distance. The method also includes maintaining the second state of the bridge portion. The method further includes implanting the pair of tines of the staple into the pair of apertures formed in the pair of biological elements. The method also includes releasing the potential energy of the elastic deformation of the second state of the bridge portion to apply a compressive force to the pair of biological elements via the tines.

In some embodiments, the method may further include forming the first pair of apertures within the pair of biological elements via a pair of openings in a drill guide portion of a guide, the pair of openings being spaced the second distance along the first direction. In some embodiments, maintaining the second state of the bridge portion may include engaging the staple with a staple engagement portion of a guide. In some embodiments, releasing the energy of the elastic deformation of the second state of the bridge portion may include disengaging the staple from the staple engagement portion of the guide.

In another aspect, the present disclosure provides a guide for a staple that is configured to apply a compressive force between biological elements. The guide includes a staple engagement portion that is operable to releasably engage and maintain an elastically deformed state of a non-linearly extending bridge portion of a staple to pre-load a compressive force between a pair of tines extending from the bridge portion and spaced a first distance.

In some embodiments, releasing the guide may further include a drill guide portion including a pair of openings spaced the first distance for facilitating the formation of a pair of apertures spaced the first distance in a pair of biological elements. In some embodiments, the guide may further include a handle portion, and the staple engagement portion and the drill guide portion may be provided at opposing longitudinal ends of the handle. In some such embodiments, the staple engagement portion and the drill guide portion may be configured for use in opposing orientations of the handle portion.

In some embodiments, the guide may further include a staple releasably engaged with the staple engagement portion such that a deformed state of a non-linearly extending bridge portion of the stable is maintained and a pair of tines extending from the bridge portion and spaced a first distance are pre-loaded in compressive. In some embodiments, the staple engagement portion may be further operable to elastically deform the bridge portion of a staple from a first state into the elastically deformed state.

These and other objects, features and advantages of this disclosure will become apparent from the following detailed description of the various aspects of the disclosure taken in conjunction with the accompanying drawings.

DETAILED DESCRIPTION

Figure 1:
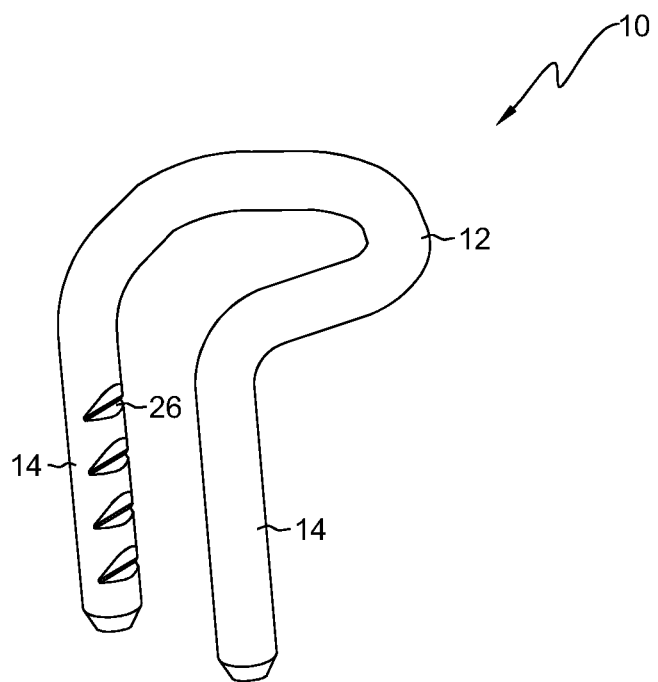
FIG. 1 illustrates a perspective view of a staple according to the present disclosure.

Each embodiment presented below facilitates the explanation of certain aspects of the disclosure, and should not be interpreted as limiting the scope of the disclosure. Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles "a," "an," "the," and "said" are intended to mean that there are one or more of the elements. The terms "comprising," "including," and "having" are intended to be inclusive and mean that there may be additional elements other than the listed elements. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein. Like reference numerals preceded by differing numerals are used throughout the figures and accompanying description of the exemplary staple embodiments of the present disclosure to indicate structurally or functionally like or similar elements, aspects, elements, components, functions, etc.

The present disclosure provides staples that provide compression to a least one biological element. The staples may be used in a wide variety of applications, including but not limited to tissue. For example, the staples described herein may be utilized across a joint or space between biological elements (e.g., tissue or bone segments) to apply compression to the joint. However, the staples may be utilized in numerous non-surgical applications where compression between a joint or the like is desired.

The staples may include an offset bridge extending between a pair of legs or tines that are inserted into tissue. The bridge may be "offset" in that it does not linearly extend between the pair of tines. Rather, the offset bridge may define a shape or pattern that allows the bridge to elastically deform or bias and thereby vary the distance between the pair of tines. In use, the bridge may be deformed before implantation from a neutral or natural state into an extended state with the distance between the pair of tines enlarged or extended (as comparted to the neutral or natural state). In situ, the tines of an elastically deformed or biased offset staple that are in the extended state may be coupled to two biological elements (e.g., two segments of hard or soft tissue) such that the bridge extends over or across a space or joint between the biological elements, and the offset staple thereby applies a compressive force to the two biological elements. When used with tissue, the closure and, potentially, compression of the space/joint between the two biological elements via the staple may facilitate fusion or healing of the biological elements.

The present disclosure also provides offset staple delivery and drill guides, as shown in FIGS. 39-43. The offset staple guides may be configured to removably couple with offset staples and elastically deform or bias the offset staples from the neutral state to the extended state to ready the staples for implantation. Some of the offset staple guides may also include a drill guide configured to facilitate the formation of apertures into biological elements for the insertion of the pair of tines of the offset staple into the biological elements. A drill guide of the offset staple guide may include multiple pairs of apertures to facilitate the formation of apertures at differing spacings that accommodate differing offset staple designs. The pair(s) of tine apertures of the drill guide portion of an offset staple guide may be spaced such that that a corresponding offset staple must be deformed or biased into an extended state for the tines to align with (and thereby insert into) apertures formed in biological elements via the tine apertures of the drill guide. The drill guide of an offset staple guide may also include one or more placement aperture and corresponding fixation or coupling member to temporarily couple the guide and at least one of the biological elements. Coupling the guide and the biological element(s) may provide for accurate formation of the tine apertures in the biological elements and on opposing sides of a space or joint between the biological elements, for example.

As shown in FIGS. 1-38, the present disclosure provides several staple embodiments that, in situ, compress two biological elements, such as, but not limited to, a junction between two biological segments, fragments or portions. The staples include an offset bridge extending between at least a pair of tines or legs that are configured to be inserted into one or more biological elements. The tines may be substantially linear, and may extend substantially parallel to each other. A free end of the tines may be pointed, angled or otherwise tapered to facilitate insertion of the tines into biological elements, as explained further below. The tines may extend for a same length along a direction between the bride and the free ends thereof (i.e., the tines include or define a same length). In other embodiments, the tines may extend for differing lengths.

The bridge is "offset" in that it does not extend linearly directly between the pair of tines. Rather, the offset bridge defines a shape or pattern as it extends between upper ends of the tines that oppose the free ends thereof, as shown in the multitude of exemplary shapes in the figures and discussed below. The pattern, pathway and/or configuration of the offset bridge may be any configuration or arrangement that allows the bridge to elastically deform to vary the distance or space between the pair of tines. The offset bridge may elastically deform or bias such that the tines are spaced further from each other as compared to a neutral or non-biased state of the staple. The offset bridge may be compressed and/or extended in the deformed or biased state as compared to the neutral state. For example, at least a portion of the bridge may be compressed, and at least another portion of the bridge may be extended or enlarged, in the deformed or base state. Such an extended or enlarged state of the tines via elastic deformation of the offset bridge may thereby provide a pre-loaded compressive force acting to "pull" or "push" (depending upon the configuration of the offset bridge) the tines closer together (i.e., to the neutral state of the staple).

In use, the offset bridge of the staple may be elastically deformed or biased into the extended state of the tines (i.e., deformed or biased such that the distance between the pair of tines is enlarged or extended from a neutral or natural position/orientation), and the tines may then be coupled to differing biological elements (e.g., differing portions of a biological segment or differing biological segments). The tines may be coupled to opposing sides of an intersection or junction of two biological elements such that the bridge extends over or across the intersection. In this way, in situ, the bridge may act to force the biological elements toward one another via the tines (i.e., exert a compressive force to the space between the biological elements). This compressive force may substantially close the space and, potentially, apply a compressive force to the closed space.

Figure 2:
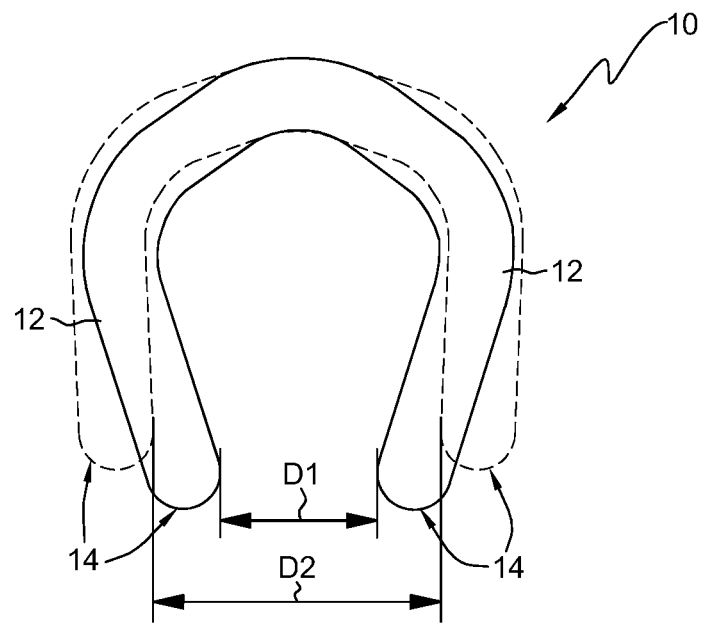
FIG. 2 illustrates a top view of the staple of FIG. 1.

As shown in FIGS. 1 and 2, in some embodiments a staple 10 according to the present disclosure may include an offset bridge 12 that may extend in a polygon like shape between the tines 14 (e.g., when viewed at a particular angle, such as along the length of the tines 14 as shown in the top view of FIG. 2). For example, at least in a first state (e.g., a neutral state) of the offset bridge 12 (shown), the offset bridge 12 may define or include a polygon-like shape as it extends between the upper ends of the tines 14, as shown in solid lines in FIG. 2. The "side" of the polygon shape extending between the tines 14 may not be provided, however (i.e., the side of the polygon shape extending between the tines 14 may be void). The bridge 12 may thereby extend or be provided on only one side of the tines 14, as shown in FIG. 2.

In the first state or neutral state of the offset bridge 12 as shown in solid lines in FIG. 2, the offset bridge 12 may space the tines 14 a first distance D1 along a direction extending linearly between the tines 14. From the first state or neutral state of the offset bridge 12 shown in solid lines in FIG. 2, the offset bridge 12 may be elastically deformed or biased into a deformed or biased state as in dashed lines in FIG. 2 that increases the distance between the tines 14 (and thereby enlarges the void therebetween). In the elastically deformed or biased state (shown in dashed lines in FIG. 2), the tines 14 may be spaced a second distance D2 along a direction extending linearly between the tines 14 that is greater than the first distance D1 the tines 14 are spaced in the first state (as shown in solid lines in FIG. 2). In the elastically deformed or biased state (as shown in dashed lines in FIG. 2), the tines 14 are thereby pre-loaded to apply a compression force between the tines 14 when the potential energy of the elastic deformation is released. The offset bridge 12 may thereby function like a resilient or spring mechanism.

In some embodiments, in the extended or biased state (as shown in dashed lines in FIG. 2) the respective angles between adjacent "sides" of the polygon shape of the offset bridge 12 may be enlarged with respect to the neutral or normal state of the bridge 12 or staple 10 (as shown in solid lines in FIG. 2). In some embodiments, in such an extended state the "sides" of the polygon shape of the offset bridge 12 may be deformed (e.g., deformed into a curved shape from a linear shape), as shown in FIG. 2. At least in the neutral state of the staple (as shown in solid lines in FIG. 2), the "sides" of the polygon shape of the bridge 12 may extend substantially linearly. The junctions or corners between the "sides" of the polygon shape of the bridge 12 may be rounded or arcuate to provide relatively smooth transitions and/or edges, as shown in FIGS. 1 and 2.

As also shown in FIGS. 1 and 2, the offset bridge 12 may be angled with respect to the tines 14. For example, the bridge 12 may extend along a plane that is angled with respect to the direction or orientation of the tines 14. The offset bridge 12 of the staple 10 shown in FIGS. 1 and 2 is oriented substantially perpendicular to the tines 14. The intersections of the bridge 12 and the pair of tines 14 may be rounded to provide relatively smooth edges therebetween and result in a spring-like bias between the tines when expanded.

The tines 14 may extend substantially linearly, as shown in FIGS. 1 and 2. For example, the tines 14 may be substantially cylindrical, although other cross-section geometries may be used (as shown in the figures and discussed below). In some embodiments, both the tines 14 and the bridge 14 may be substantially circular or elliptical in cross-section, as shown in FIGS. 1 and 2. As also shown in FIGS. 1 and 2, the tines 14 may include indentations, ridges, ramps, barbs, or surface roughness features, finishes, textures or other engagement mechanisms 26. The engagement mechanism 26 of the tines 14 may at least be provided at least on the surfaces of the tines 14 that are adjacent and face each other (i.e., face an intermediate or central portion of the staple 10). In this way, in situ, the portion of the tines 14 that acts against the biological elements to compress the biological elements when the pre-load of the bridge 12 is released may include the engagement mechanism 26. The engagement mechanism 26 of the tines 14 may act to grip or otherwise increase friction between the biological elements and the tines 14. The engagement mechanism 26 may thereby act to prevent removal of the staple 10 from the biological elements after implantation.

Figure 3:
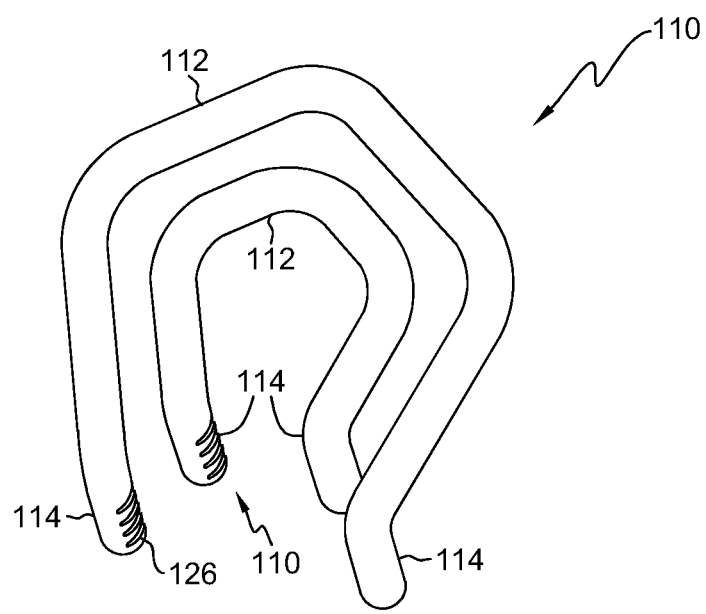
FIG. 3 illustrates a perspective view of nesting staples according to the present disclosure.
Figure 4:
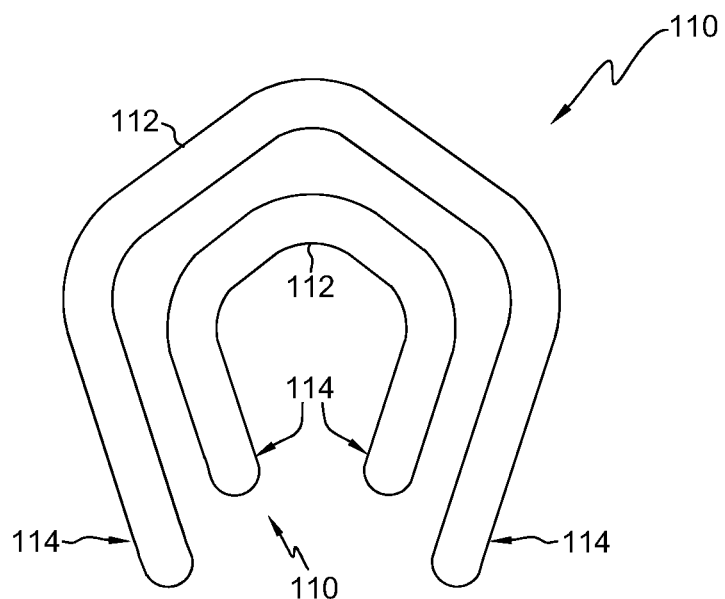
FIG. 4 illustrates a top view of the nesting staples of FIG. 3.
Figure 5:
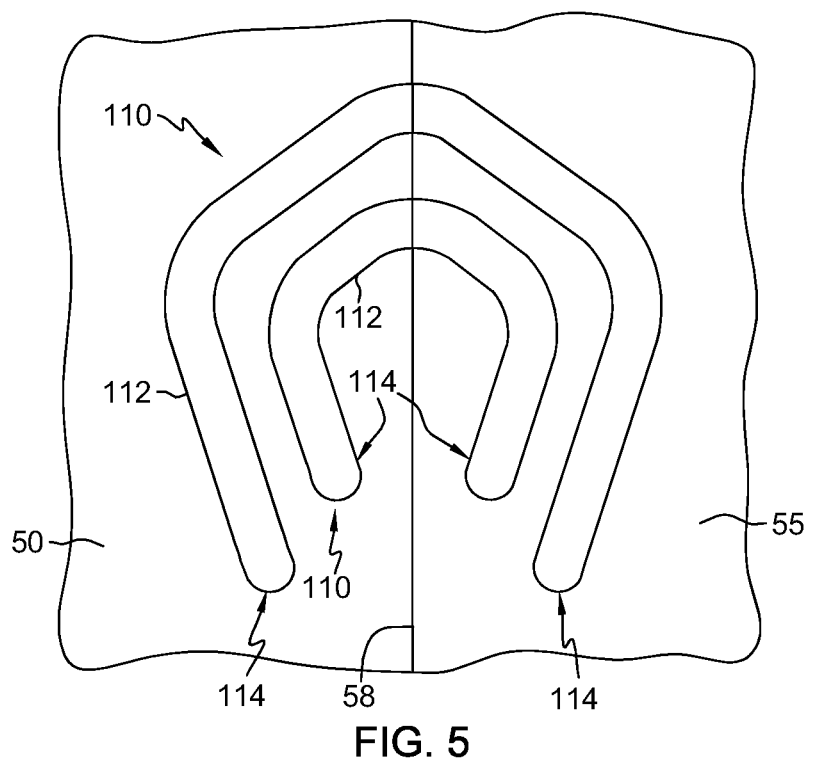
FIG. 5 illustrates a top view of the nesting staples of FIG. 3 implanted into biological elements.

In some embodiments, as shown in FIGS. 3-5, the staples 110 according to the present disclosure may be nestable or stackable to allow larger contact area and more force across a space between biological elements. Specifically, multiple staples 110 may be configured to be nestable or stackable, such as overlapped, staggered, concentric, intermingled or otherwise provided within an area smaller than if the staples 110 were positioned adjacent each other, as shown in FIGS. 3-5. In this way, multiple staples 110 can be utilized within a relatively small area to reduce and, potentially, compress a space between biological elements. In the embodiment shown in FIGS. 3-5, the staples 110 may be differing sizes of a polygon shape such that a relatively small polygon shaped staple 110 is able to fit within the boundary of a relatively large polygon shaped staple 110.

As shown in FIG. 5, one tine 114 of each of the nested or stacked staples 110 may be implanted into a first biological element 50 (e.g., a biological segment or fragment) on one side of a space, junction or joint 58 (graphically represented by a vertical line) and the other tine 114 of each staple 110 may be implanted in a second biological element 55 on an opposing side of the space or junction 58 such that each offset bridge 112 spans across the space or junction 58. Before implantation into the adjacent biological elements 50, 55, the offset bridges 112 of the staples 110 may be elastically deformed or biased (e.g., extended and/or compressed) so that the distance between the pairs of tines 114 is enlarged or extended as compared to a neutral or natural position/orientation of the offset staples 110 (i.e., an extended state). The staples 110 may be implanted in the pre-loaded or deformed extended state such that, in situ, as shown in FIG. 5, the offset staples 110 apply a compressive force to the biological elements 50, 55 across the junction or space 58. The compressive force to the biological elements 50, 55 across the junction 58 may act to substantially close a space between the biological elements 50, 55 (if present) and, potentially, apply a compression force to the junction 58 to facilitate fusion of the biological elements 50, 55.

Figure 6:
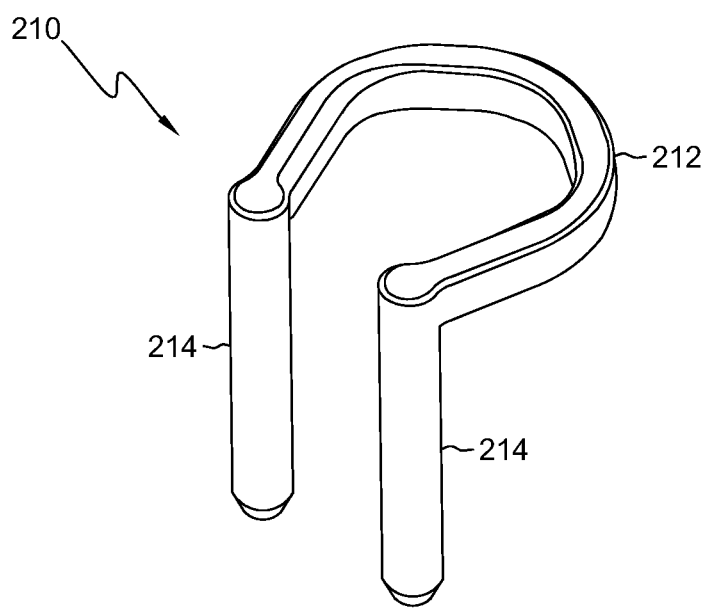
FIG. 6 illustrates a perspective view of another staple according to the present disclosure.

As shown in FIG. 6, in some embodiments the offset bridge 212 of a staple 210 according to the present disclosure may form a rounded pentagon or horseshoe like shape. For example, at least one of the "sides" of the pentagon shape may be arcuate, radiused or rounded. As another example, the tines 214 of the staple 210 may extend out from the "sides" of the shape or pattern of the offset bridge 212. In some embodiments, the tines 214 may be substantially circular or elliptical in cross-section, and the bridge 212 may be substantially rectangular, square or other cross-sectional shape with substantially linear or planar sides, as shown in FIG. 5.

Figure 7:
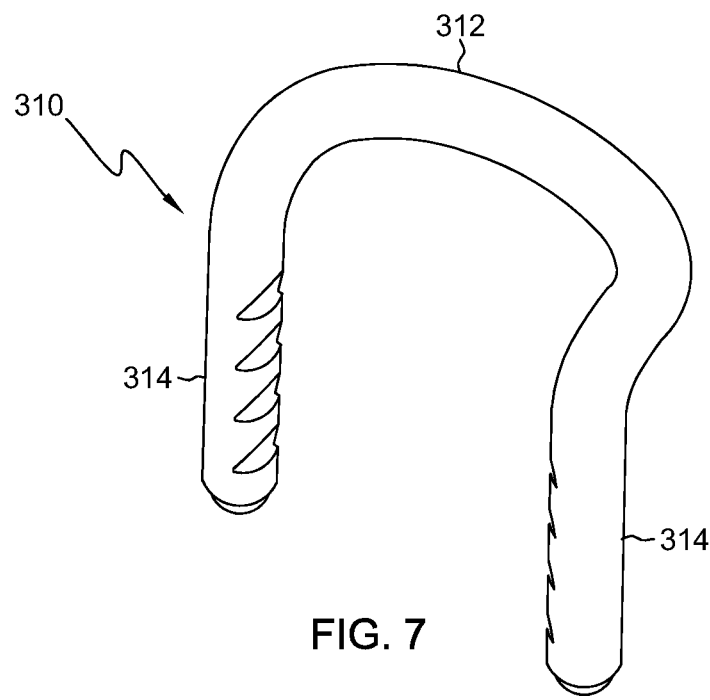
FIG. 7 illustrates a perspective view of another staple according to the present disclosure.
Figure 8:
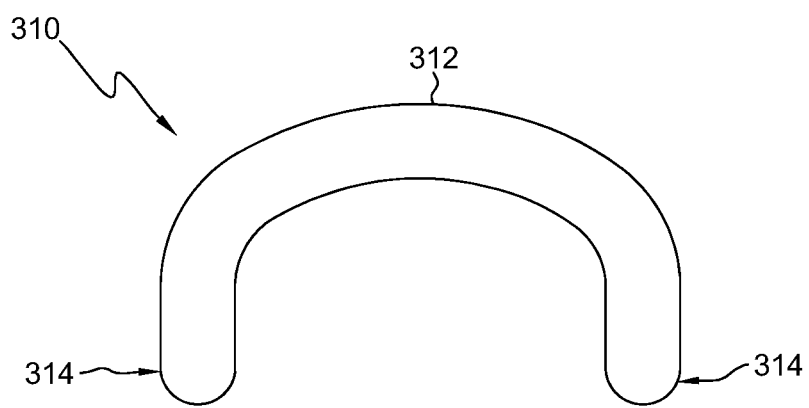
FIG. 8 illustrates a top view of the staple of FIG. 7.

As shown in FIGS. 7 and 8, in some embodiments the offset bridge 312 of a staple 310 according to the present discourse may form a truncated pentagon-like or horseshoe-like shape (e.g., when viewed along the direction of the tines 314, as shown in the top view of FIG. 8). For example, the offset bridge 312 may form half or a portion of a pentagon or "C" shape. In some such embodiments, the offset bridge 312 may form half or a portion of the pentagon shape of the offset bridge 12 of the exemplary staples 10 and 110 shown in FIGS. 1-5, or half or a portion of the rounded pentagon shape of the offset bridge 210 of the exemplary staple 210 shown in FIG. 6.

Figure 9:
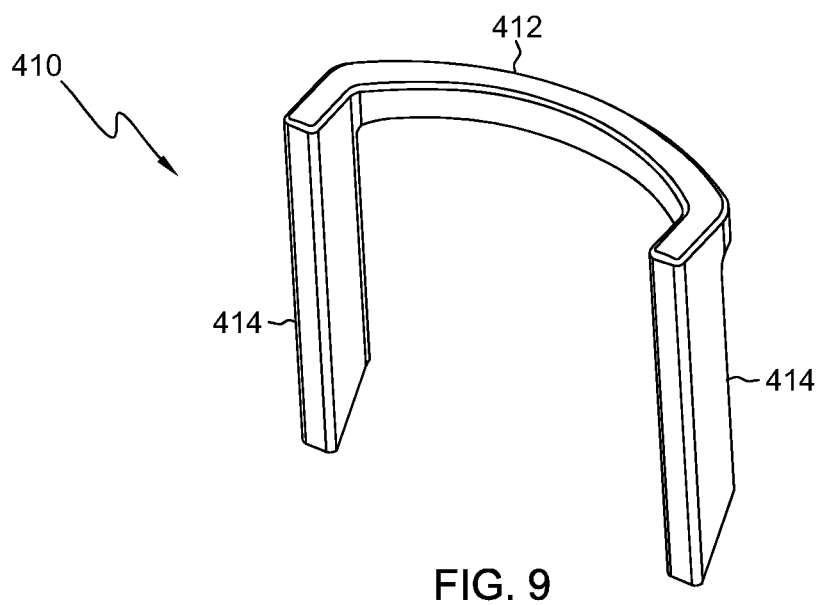
FIG. 9 illustrates a perspective view of another staple according to the present disclosure.

As shown in FIG. 9, in some embodiments the offset bridge 412 of a staple 410 according to the present disclosure may form a radiused or arcuate shape. For example, the offset bridge 412 of a staple 410 may extend in a substantially elliptical path or shape between the tines 414, as shown in FIG. 9. As also shown in FIG. 9, the tines 414 may be substantially rectangular in cross-section or otherwise include at least one substantially planar surface. In some embodiments, the cross-section of both the tines 414 and the bridge 412 may be substantially rectangular, square or other cross-sectional shape that includes substantially linear or planar sides.

Figure 10:
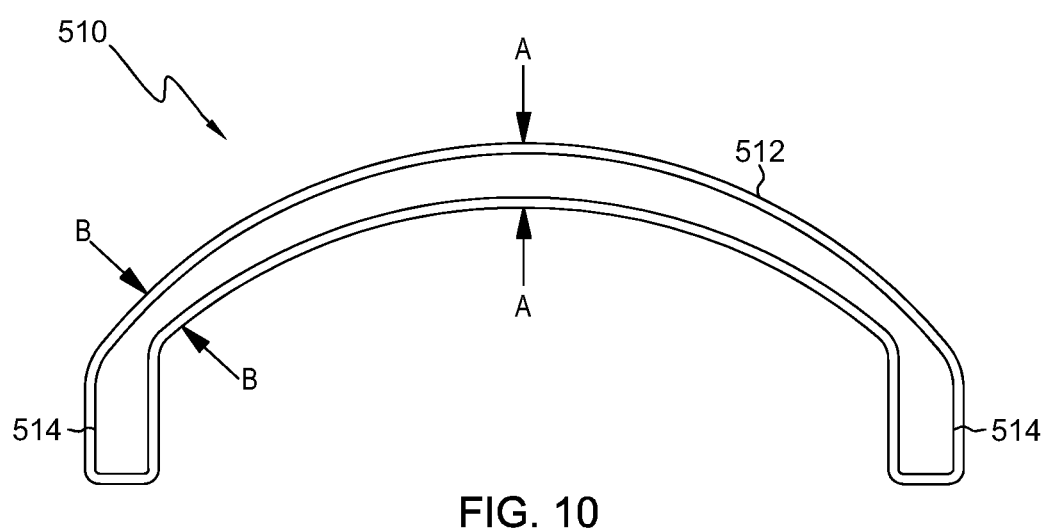
FIG. 10 illustrates a top view of another staple according to the present disclosure.

As shown in the top view of FIG. 10, in some embodiments the offset bridge 514 of a staple 510 according to the present disclosure may vary in thickness or cross-sectional size as it extends between the tines 514. For example, the profile of the offset bridge 512 may be of variable cross-section for optimal stress distribution and elasticity. As shown in FIG. 10, the variable cross-section of the offset bridge 514 may be smaller in size proximate to the tines 514 as indicated by the arrows "B" than in an intermediate portion of the bridge 514 as indicated by the arrows "A". In some embodiments, the variable cross-section of the offset bridge 514 may be expand in size from proximate to the tines 514 to an intermediate portion of the bridge 514.

Figure 11:
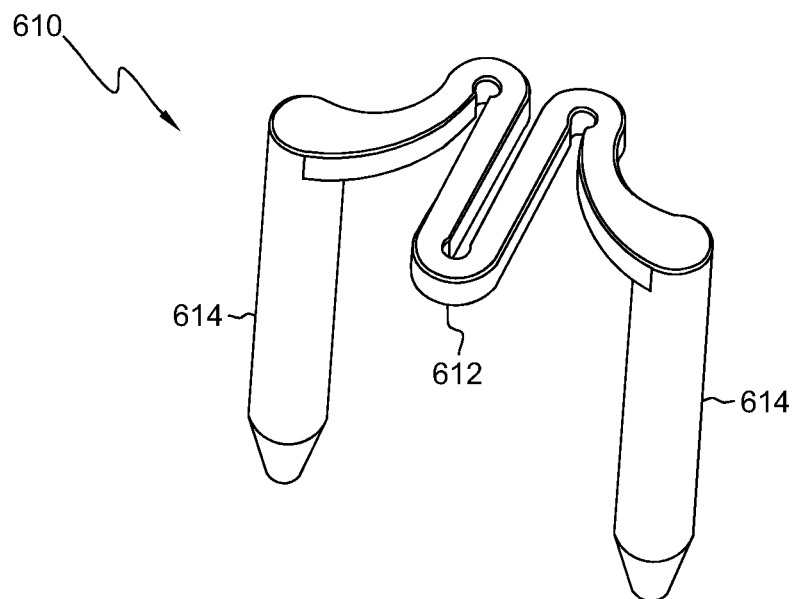
FIG. 11 illustrates a perspective view of another staple according to the present disclosure.

As shown in FIG. 11, in some embodiments of a staple 610 according to the present disclosure the offset bridge 612 may form a shape that allows a relatively high amount of deflection of the bridge 612 in an extended state, such as in comparison to the amount of space between the tines 614 in the neutral state. For example, as shown in FIG. 11 the bridge 612 may form an "M" shape that substantially increases the potential elastic deformation of the bridge 614, and thereby the travel or space between the tines 614 in the extended state of the staple 610. The bridge 612 may form the "M" shape as it extends between the tines 614 such that a portion of the bride 612 is positioned on one side of the tines 614 and another portion of the bride 612 is positioned on the opposing side of the tines 614, as shown in FIG. 11.

Figure 12:
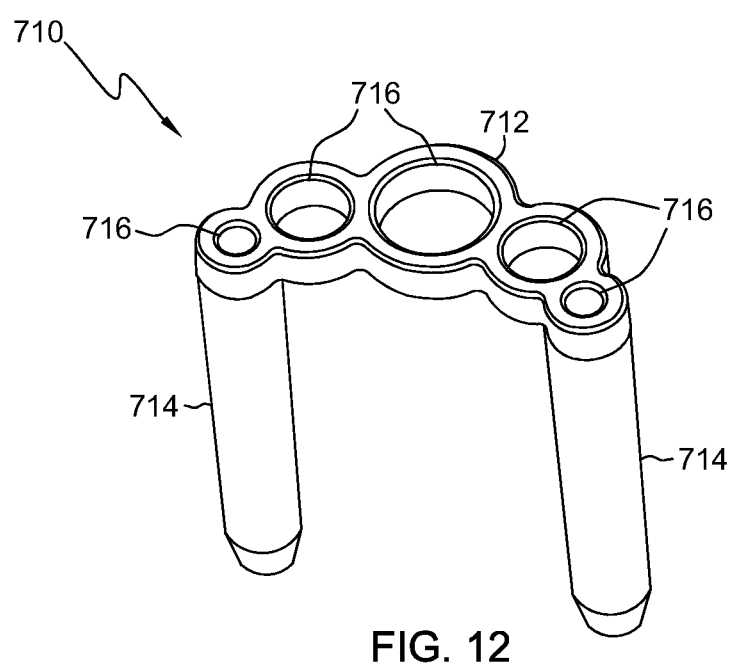
FIG. 12 illustrates a perspective view of another staple according to the present disclosure.
Figure 13:
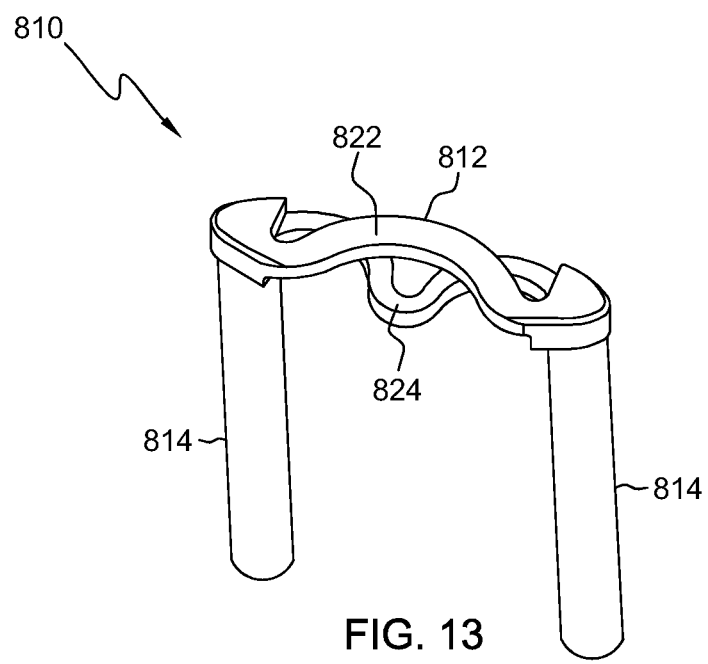
FIG. 13 illustrates a perspective view of another staple according to the present disclosure.
Figure 14:
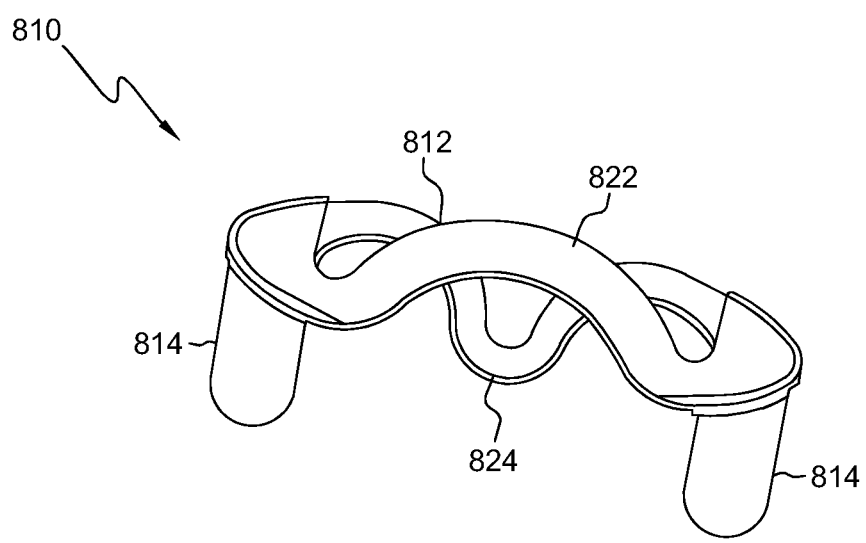
FIG. 14 illustrates an elevational perspective view of the staple of FIG. 13.
Figure 15:
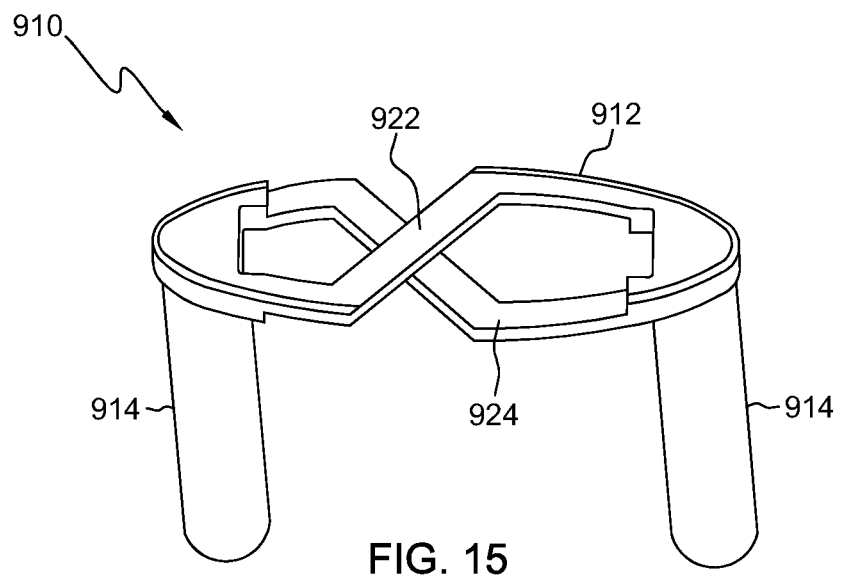
FIG. 15 illustrates a perspective view of another staple according to the present disclosure.

As shown in FIG. 12, in some embodiments of a staple 710 according to the present disclosure the offset bridge 712 may include or form at least one aperture 716 extending therethrough. The at least one aperture 716 extending through the bridge 712 may allow, or provide for, deformation of the bridge 712. For example, as shown in FIG. 12 the bridge 712 may form a series of apertures 716 arranged in an arc between the tines 714 to provide for a greater degree of elastic deformation of the bridge 712 (and/or a lower modulus of elasticity) than compared to if the apertures 716 were not provided.

Figure 16:
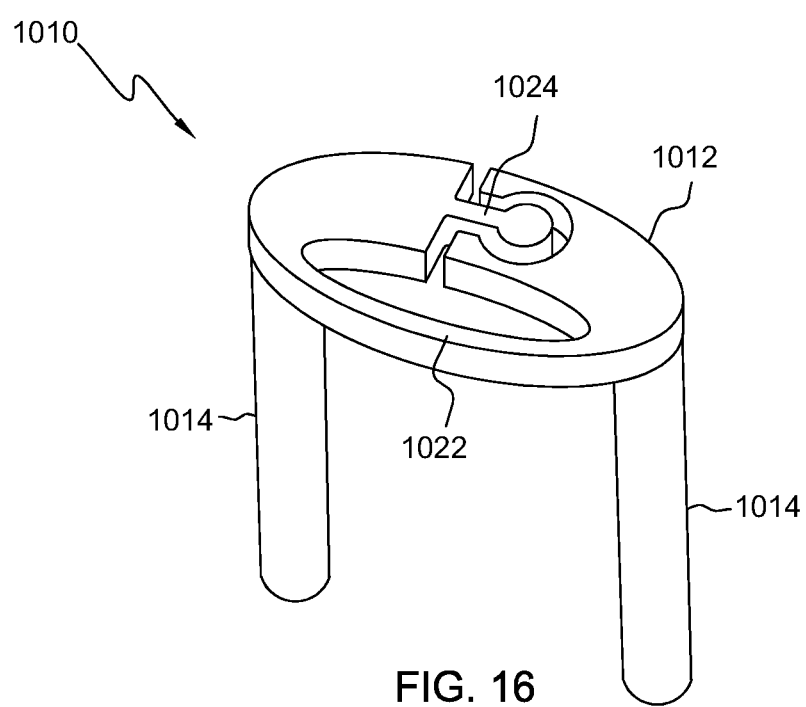
FIG. 16 illustrates a perspective view of another staple according to the present disclosure.

As shown in the exemplary staples 810, 910 and 1010 of FIGS. 13-16, in some embodiments according to the present disclosure the offset bridge 812, 912, 1012 may include multiple portions or elements that extend non-linearly at least partially between the tines 814, 914, 1014. In some embodiments, the distinct portions of the offset bridge 810, 912 may overlap each other as they extend between the pair of tines 814, 914, as shown in the staple 800 of FIGS. 13 and 14 and the staple 910 of FIG. 15. As also shown in the staple 800 of FIGS. 13 and 14 and the staple 910 of FIG. 15, in some embodiments the staples 800, 900 may include a pair of portions 822, 824, 922, 924 that extend at least partially between the tines 814. As shown in FIG. 16, in some embodiments the offset bridge 1012 may include a first portion 1022 that deforms and allow the tines 1014 to move to the extended state of the staple 1010, and a second portion or feature 1024 that is operable to limit the amount of deformation (i.e., expansion/contraction) of the first portion of the bridge 1012 (and thereby the travel of the tines 1014).

Figure 17:
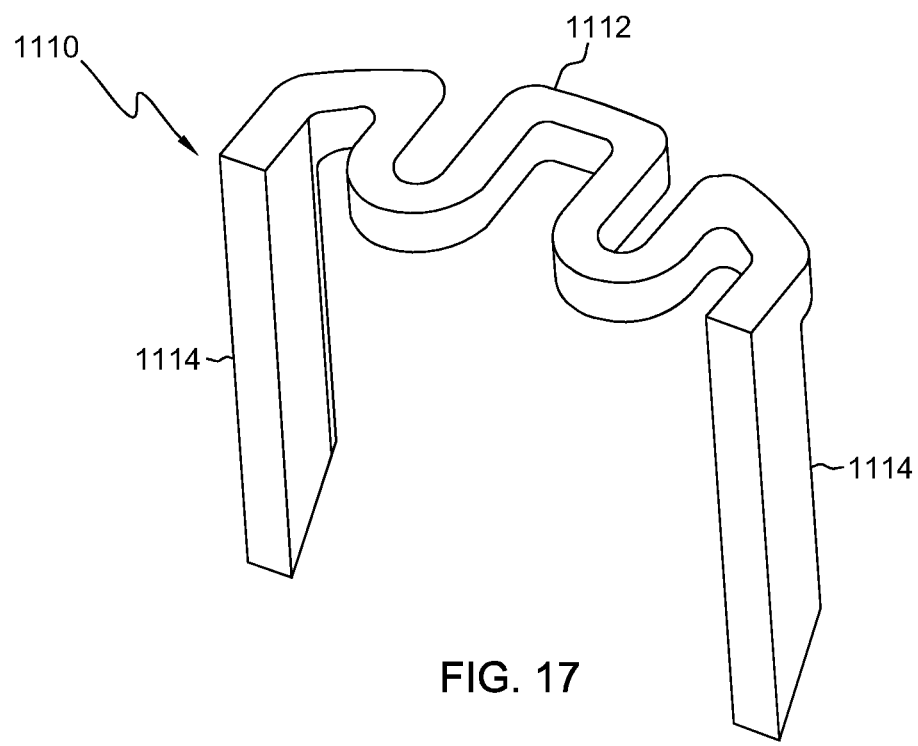
FIG. 17 illustrates a perspective view of another staple according to the present disclosure.
Figure 18:
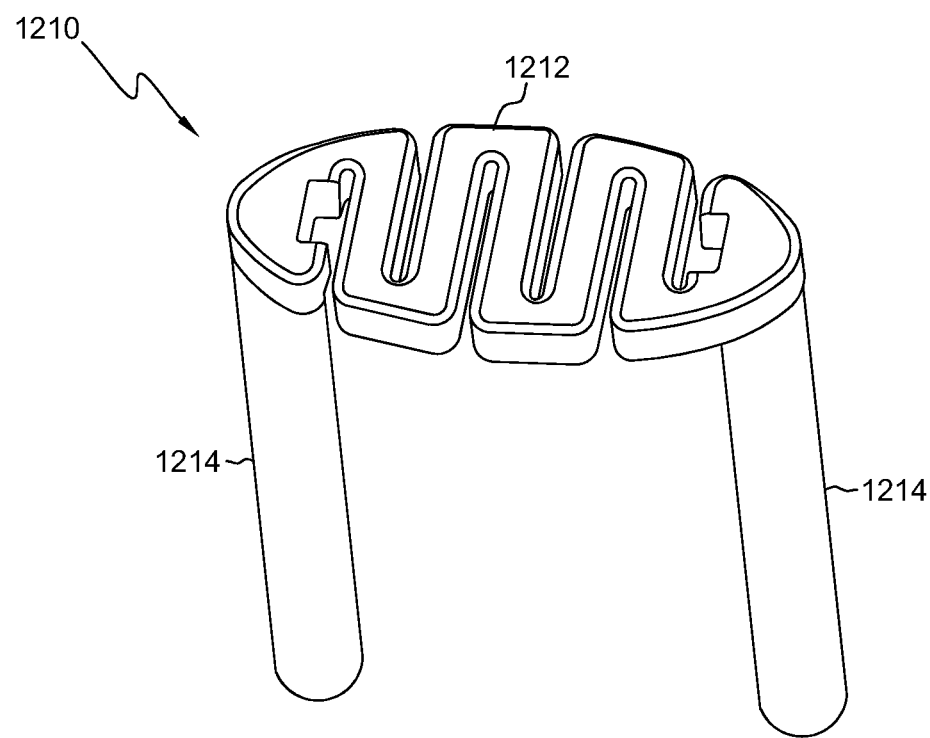
FIG. 18 illustrates a perspective view of another staple according to the present disclosure.

As shown in the exemplary staple 1110 of FIG. 17 and the exemplary staple 1210 of FIG. 18, in some embodiments according to the present disclosure, the offset bridge 1112, 1212 may include or define a geometric shape that creates a longer effective length that provides for added or additional deflection of the offset bridge 1112, 1212 (e.g., as compared to other shapes or configurations). For example, as shown in FIGS. 17 and 18 the bridge 1112, 1212 may serpentine, zigzag, or mimic a compression spring-shape as it extends between the tines 1114, 1214. In this way, the "true" or actual length of the offset bridge 1112, 1212 may be significantly greater than the "net" length of the bridge 1112, 1212 measured linearly between the tines 1114, 1214, and allow for a relatively high degree or amount of flexion and thereby expansion of the tines 1114, 1214 in the extended state of the staple 1110, 1210.

Figure 19:
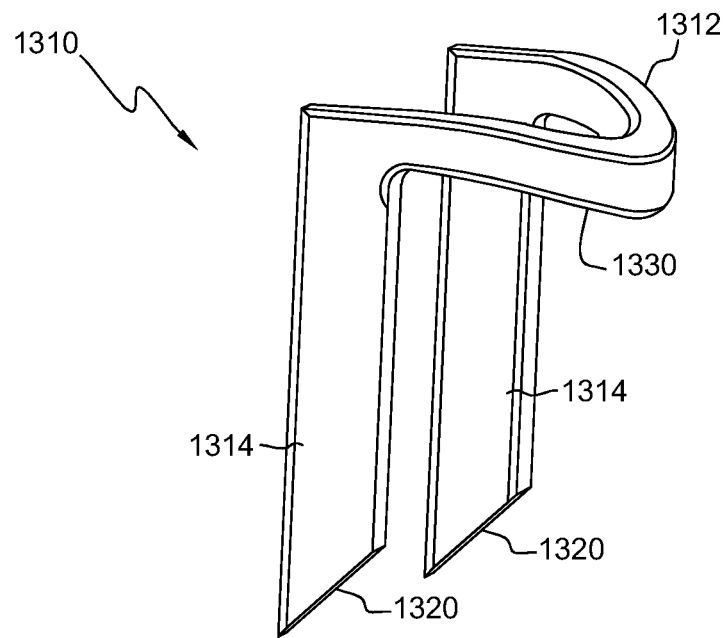
FIG. 19. illustrates a perspective view of another staple according to the present disclosure.
Figure 20:
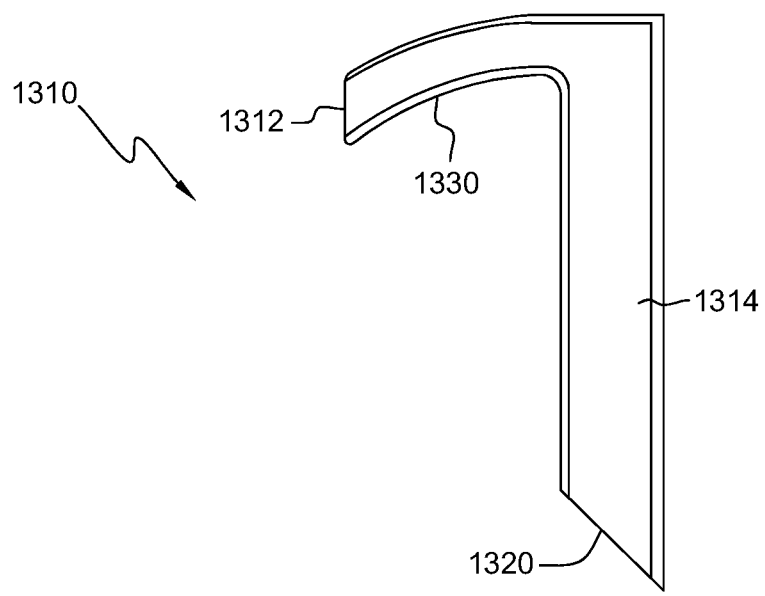
FIG. 20. illustrates a side view of the staple of FIG. 19.

As shown in FIGS. 19 and 20, in some embodiments of a staple 1310 according to the present disclosure the offset bridge 1312 may extend in a non-planar direction as it extends between the tines 1314. For example, as shown in FIGS. 19 and 20, the offset bridge 1312 may be curved or angled downward toward free ends 1320 of the tines 1314 as it extends between the tines and away from the top or upper portions of the tines 1314 opposing the free ends 1320 of the tines 1314. In some such embodiments, the offset bridge 1314 may be positioned substantially on one side of the tines 1314, as shown in FIG. 20. The bottom surface 1330 of the offset bridge 1312 that faces the free ends 1320 of the tines 1314 may be shaped to substantially match the shape and abut, or penetrate, the biological elements in which the tines 1314 of the staple 1310 may be implanted. For example, if the outer surface of particular biological elements are curved or pointed (such as rounded bone segments), the bottom surface 1330 of the offset bridge 1312 may be likewise curved or arcuate (e.g., convex) as it extends away from the side of the tines 1314 to substantially match the shape and abut the biological elements. In this way, the staple 1310 may define a low profile when implanted.

Figure 21:
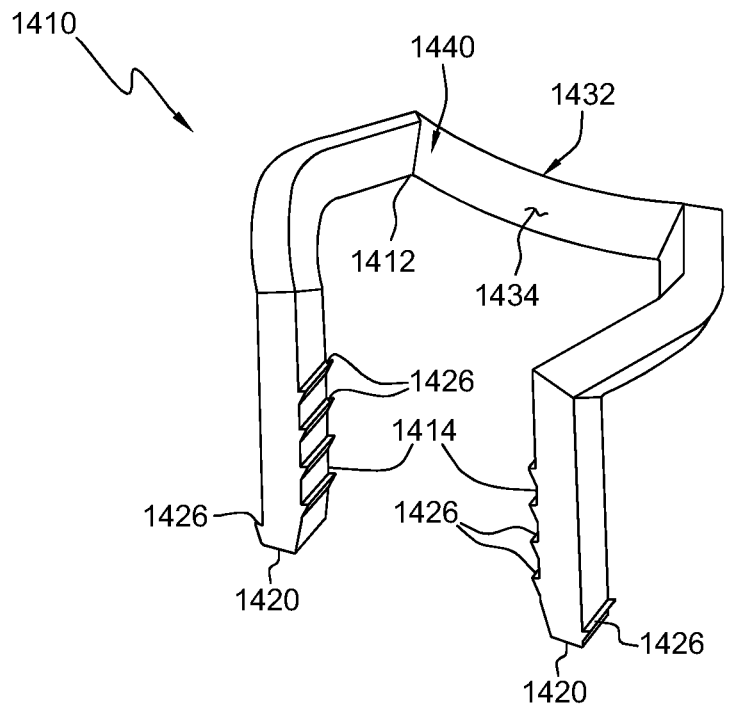
FIG. 21 illustrates a perspective view of another staple according to the present disclosure.
Figure 22:
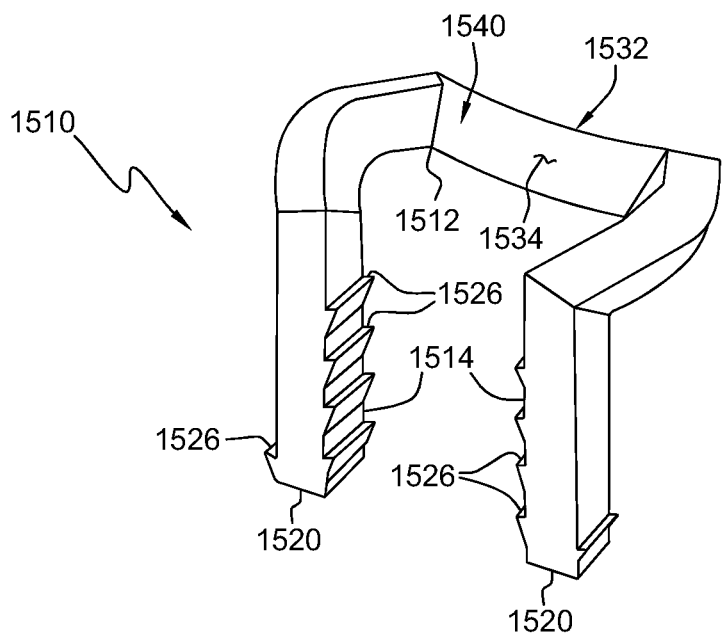
FIG. 22 illustrates a perspective view of another staple according to the present disclosure.
Figure 23:
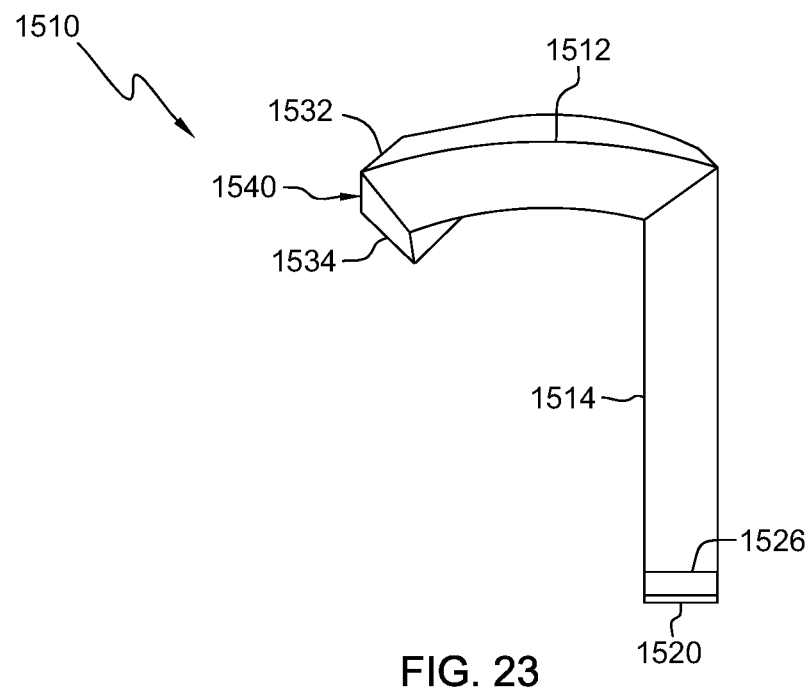
FIG. 23. illustrates a side view of the staple of FIG. 22.

As shown in the exemplary staple 1410 of FIG. 21 and the exemplary staple 1510 of FIGS. 22-25, in some embodiments a cross-section of at least one of the tines 1414, 1514 and the bridge 1412, 1512 may define a substantially square, rectangular or other cross-sectional shape that defines at least one substantially linear or planar outer surface or side in cross-section. As also shown in FIGS. 21 and 22-25, the bridge member 1412, 1512 may be oriented such that at least one linear or planar side in cross-section is not oriented substantially perpendicular or substantially parallel to the direction that the tines 1414, 1514 extend away from the bridge member 1412, 1512. Rather, the bridge 1412, 1512 may be oriented such that at least one of a linear or planar side in cross-section is angled with respect to the direction the tines 1414, 1514 extend away from the bridge member 1412, 1512 (e.g., angled with respect to linear or planar side of the tines 1414, 1514). For example, a top surface 1432, 1532 of the bridge 1412, 1512 may be planar in cross-section and angled downwardly as it extends away from a side of the tines 1414, 1514, as shown in FIG. 23. As another example, an inner surface 1434, 1534 of the bridge 1412, 1512 may be planar in cross-section and angled downwardly toward the free ends 1420, 1520 of the tines 1414, 1514 as it extends from the top surface 1432, 1532 and toward the tines 1414, 1514, as shown in FIGS. 21 and 23.

Figure 24:
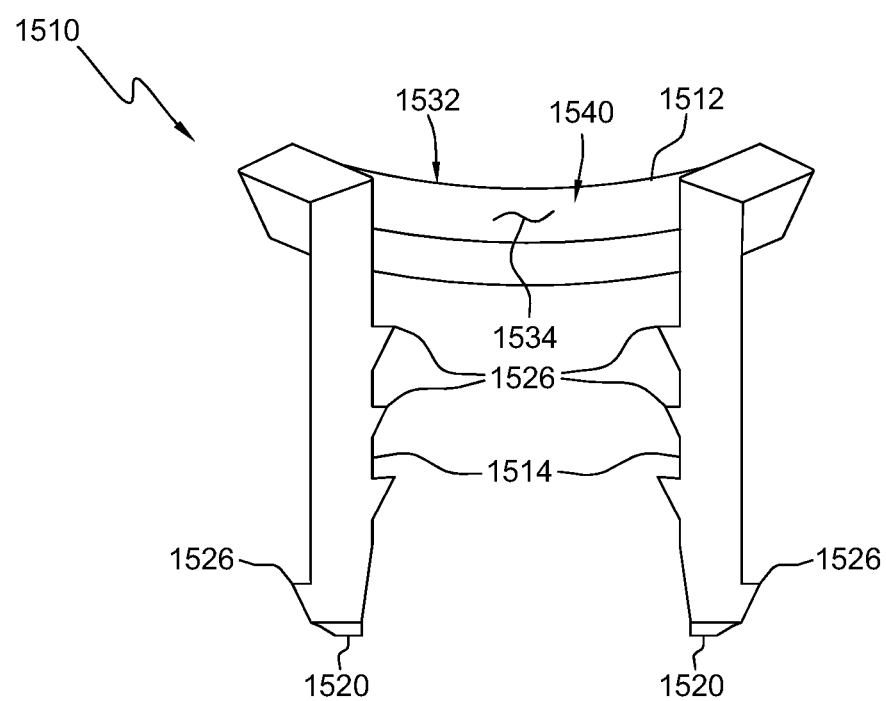
FIG. 24. illustrates a back view of the staple of FIG. 22.
Figure 25:
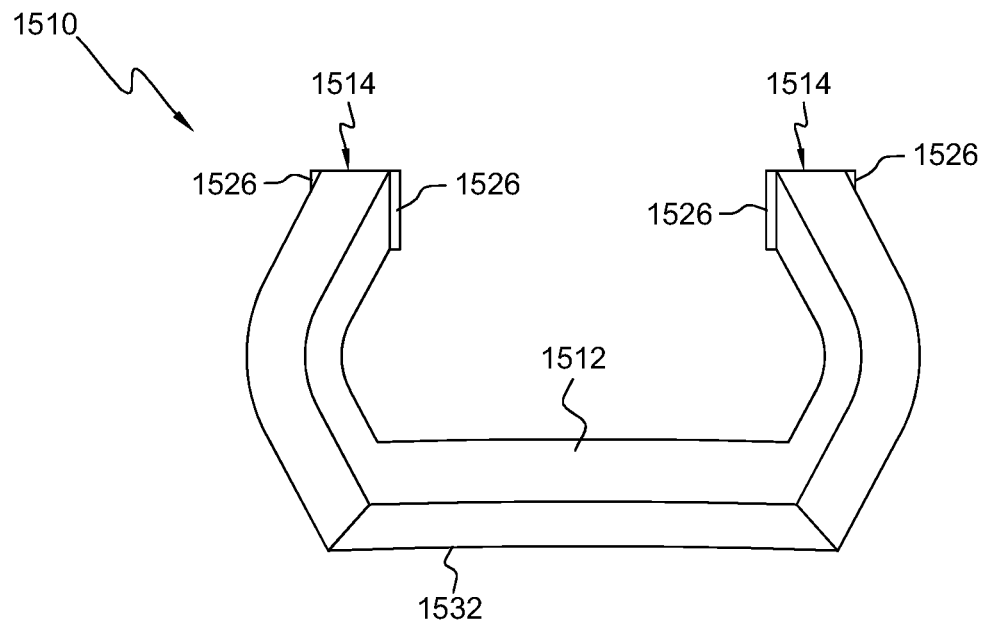
FIG. 25. illustrates a top view of the staple of FIG. 22.
Figure 26:
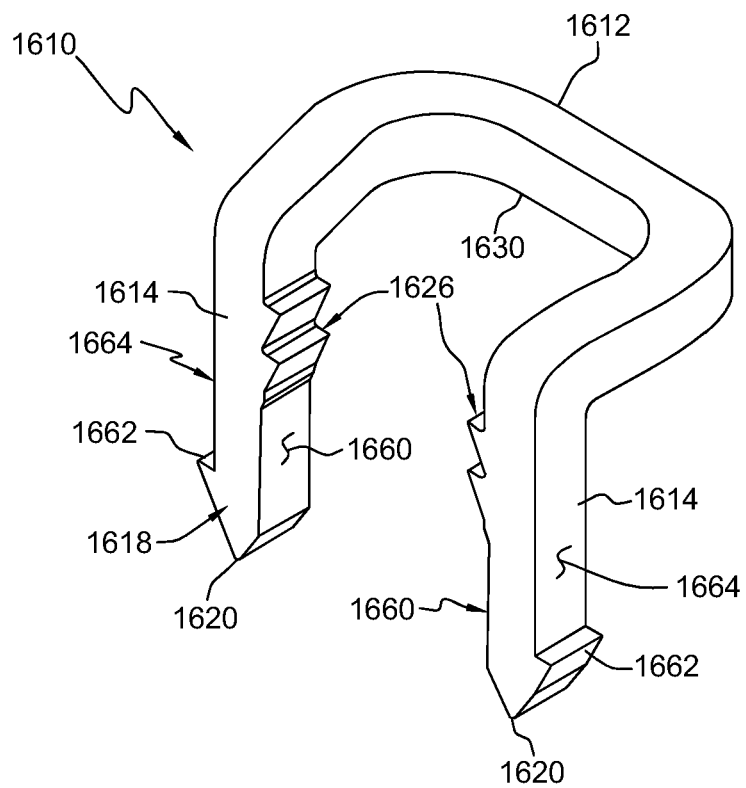
FIG. 26. illustrates a perspective view of another staple according to the present disclosure.

As also shown in FIGS. 21 and 22-25, the staples 1410, 1510 may from a hexagon like shape (e.g., when viewed from above as shown in FIG. 25). A side portion or segment 1440, 1540 of the bridges 1412, 1512 forming the side of the hexagon shape spaced furthest from the tines 1414, 1514 may be bowed or convex downwardly toward the free ends 1420, 1520 of the tines 1414, 1514 as it extends away from the tines 1414, 1514, as shown in FIGS. 21 and 24. Further, the sides or portions of the bridges 1412, 1512 extending between the tines 1414, 1514 and the side portion 1440, 1540 may also be non-planar. As shown in FIGS. 21 and 23, the sides or portions of the of the bridges 1412, 1512 extending between the tines 1414, 1514 and the side portion 1440, 1540 may initially extend upwardly away from the free ends 1420, 1520 of the tines 1414, 1514 as they extend away from tines 1414, 1514, and then extend therefrom downwardly toward the free ends 1420, 1520 of the tines 1414, 1514 as they extend to the side portion 1440, 1540.

Figure 27:
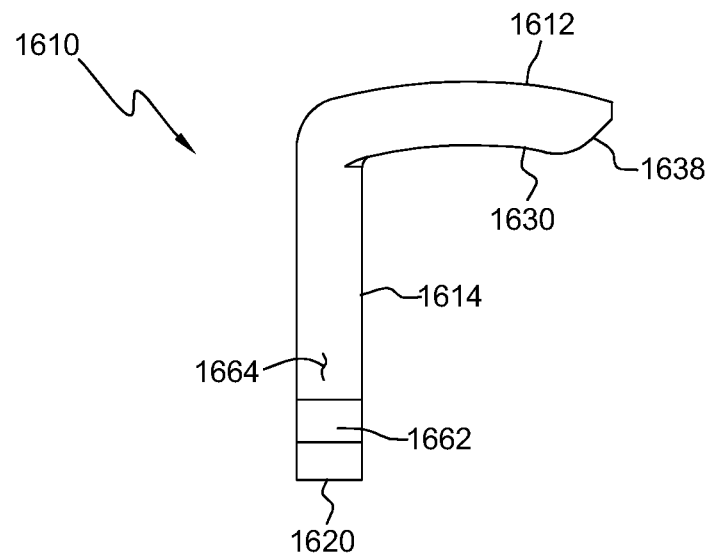
FIG. 27. illustrates a side view of the staple of FIG. 26.
Figure 28:
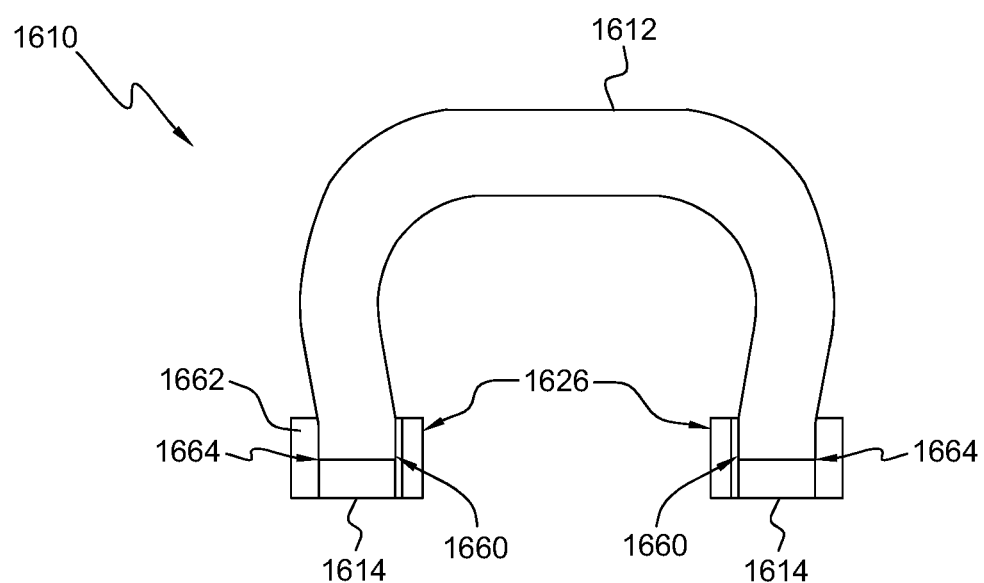
FIG. 28. illustrates a top view of the staple of FIG. 26.
Figure 29:
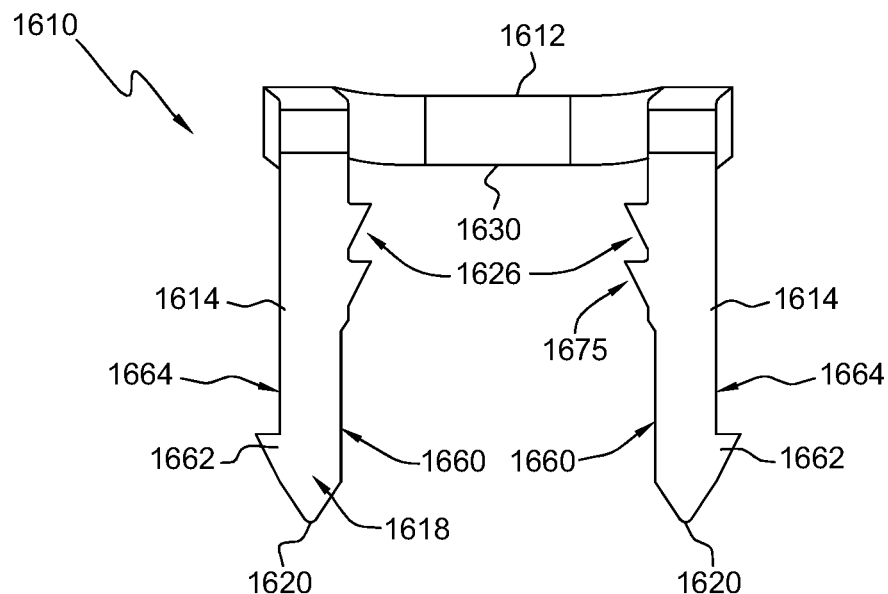
FIG. 29. illustrates a back view of the staple of FIG. 26.
Figure 30:
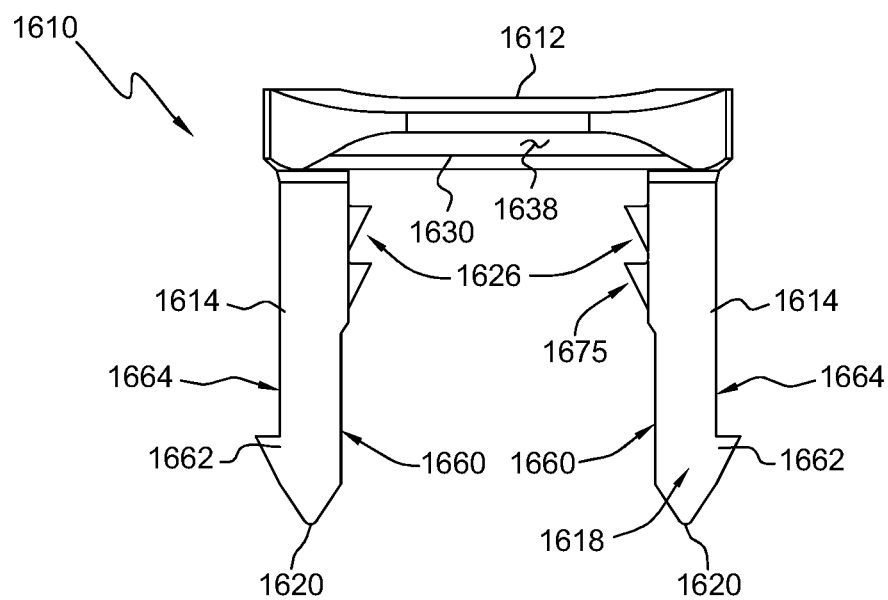
FIG. 30. illustrates a front view of the staple of FIG. 26.

Another exemplary staple 1610 according to the present disclosure is shown in FIGS. 26-31. As shown in FIGS. 26-31, the staple 1610 may include a horseshoe or "U" shaped bridge 1612. The offset bridge 1612 may extend from one side of the tines 1614 and form an arcuate or curved profile when viewed form a longitudinal side of the staple 1610, as shown in FIG. 27. An outer portion of the bridge 1612 (e.g., a portion positioned furthest from the tines 1614 along a first side) may include a relief or angled profile 1638 extending from a bottom surface 1630 of the bridge 1612, as shown in FIGS. 27 and 30.

The engagement mechanism 1626 disposed on the tines 1614 of the staple 1610 may be barbs or similar shaped projections configured to engage biological elements and to increase the compressive load of the tines 1614 and/or barbs 1626 to the biological elements as compared to tines 1614 or engagement mechanism 1626 of prior staples, as shown in FIGS. 26-31. As described above, the offset bridge 1612 may be elastically deformed in an extended stat prior to implantation of the tines 1614 in the biological elements such that the bridge 1612 is preloaded to apply a compression force to the tines 1614 (i.e., the preload acts in a direction that tends to forces or bias the tines 1614 closer to one another). After implantation of the staple 1610, the preload of the bridge 1612 may be released such that the bridge 1614 is free to elastically deform toward its original shape or natural state to thereby force the tines 1614 towards one another. In this way, once the staple 1610 in implanted and the preloaded bridge 1612 is "released," the tines 1614 apply a compressive force to the biological elements to reduce any space between the biological elements and, potentially, apply a compressive force to the junction between the biological elements (i.e., apply a compressive force to whatever is positioned in the interior of the staple 1610 between the tines 1614).

Figure 31:
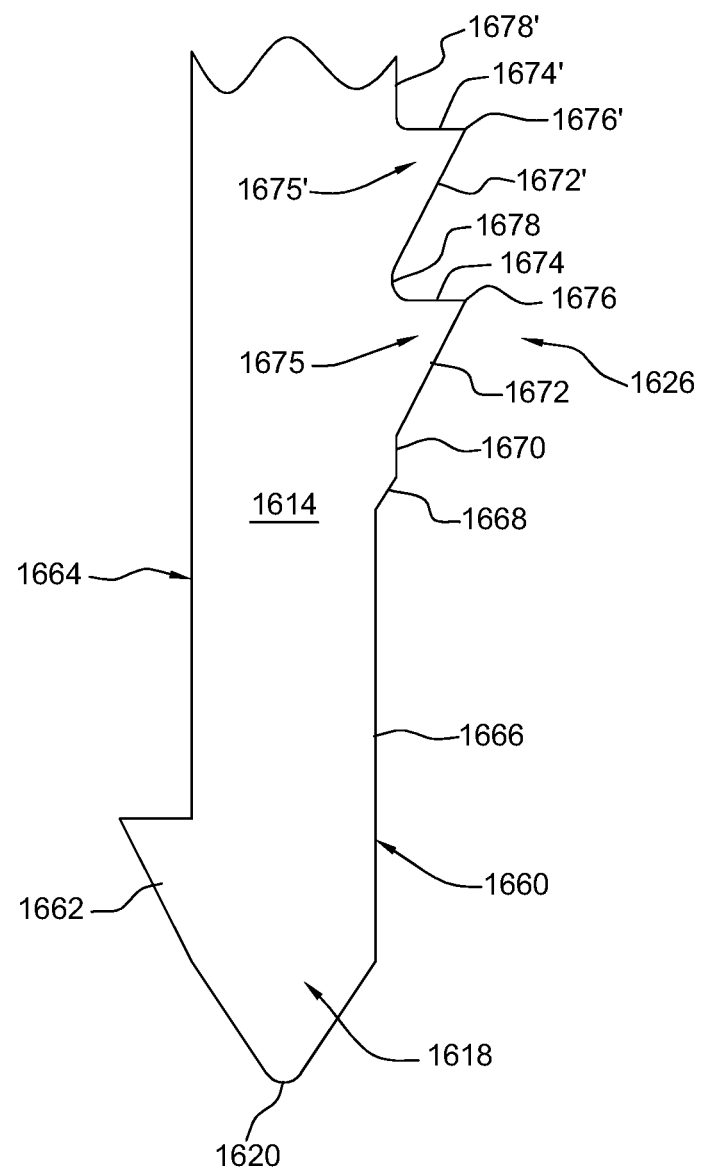
FIG. 31. illustrates an enlarged front or back view of a portion of a tine of the staple of FIG. 26.

FIG. 31 is an enlarged front/rear side view of a tine 1614 of the staple 1610. Although only one tine 1614 is illustrated in FIG. 31, each of the tines 1614 of the staple 1610 may include such a configuration or arrangement, as depicted in FIGS. 26-30. The configuration of the tines 1614 may be utilized with any bridge of the stapled discussed above (or any other stable bridge), such as, but not limited to, any of the offset bridge configurations described herein. As shown in FIGS. 26-31, the tines 1614 of the staple 1610 may include an interior planar surface or portion 1660 that substantially faces towards the other opposing tines 1614 of the staple 1610 (i.e., faces towards the interior of the staple 1610), such as along a longitudinal direction, as shown in FIGS. 26 and 28-30. The tines 1614 may include a barb-like structure 1662 extending from an outer side 1664 of the tines 1614 that substantially opposes the interior surface 1660 and substantially faces away from the other opposing tines 1614 of the staple 1610 (i.e., faces away the interior of the staple 1610). The tines 1614 may also define or form an end portion 1618 that includes the free end 1620 of the tines 1614. In this way, the tines 1614 may form a cantilever structure.

As noted above, in situ, a pair of tines 1614 may exert a compressive force to biological elements or any other material that is positioned substantially between the tines 1614. In this way, the interior surface 1660 of the tines 1614 may abut or otherwise transfer at least some of the compressive forces to the biological elements during use. The interior surface 1660 of the tines 1614 of the staple 1610 shown in of FIGS. 26-31, such as the engagement mechanisms 1626, may be operable to increase the compressive load of the staple 1610 as compared to previous tines and staples.

Although FIGS. 26-31 depict the interior surface 1660 of the tines 1614 as including or defining substantially linear or planar portions, the interior surface 1660 of the tines 1614 may also include or define one or more non-linear or non-planar portion (e.g., an arcuate edge or surface). As shown in FIG. 31, the interior surface 1660 of the tines 1614 may also include a first surface or portion 1666 that is proximate or adjacent the end portion 1618 of the tines 1614. The first portion 1666 may be substantially planar. The first portion 1666 of the interior surface 1660 may extend substantially vertically (e.g., when the tines 1614 are oriented substantially vertically). In an alternative embodiment, the first portion 1666 of the interior surface 1660 of the tines 614 may be angled inwardly towards the other opposing tine 1614 of the staple 1610 as it extends away from the end portion 1618 and towards the bridge 1612.

The engagement mechanism 1626 may include a first ramp or sloped portion 1668 of the interior surface 1660 that extends from the first portion 1666 of the interior surface 1660 of the tines 1614, as shown in FIG. 31. The first ramp portion 1668 may also be angled inwardly towards the other opposing tine 1614 of the staple at it extends away from the first portion 1666 and towards the bridge 1612. In some embodiments 1610, the first ramp portion 1668 may be angled inwardly towards the other opposing tine 1614 at an angle within the range of about 20 degrees to about 30 degrees as it extends away from the first portion 1666 and towards the bridge 1612. In some embodiments (not shown), if the first portion 1666 is angled inwardly towards the other opposing tine 1614 of the staple 1610 at it extends away from the end portion 1618 and towards the bridge 1612, the first ramp portion 1668 may be angled inwardly at a greater angle or degree than the first portion 1666 to facilitate load transfer of the compressive of the tines 1614 to the biological elements.

Extending from the first ramp portion 1668, the interior surface 1660 and engagement mechanism 1626 of the tines 1614 may further include a plateau portion 1670. The plateau portion 1670 may be substantially planar and may extend substantially vertically (e.g., when the tines 1614 are oriented substantially vertically), as shown in shown in FIG. 31. However, the plateau portion 1670 may also be angled with respect to vertical. The plateau portion 1670 may be positioned further inwardly (towards the other tine 1614 of the staple 1610) than the first portion 1666. In this way, the first ramp portion 1668 may provide a transition length or "ramp" between the first portion 1666 and the inwardly-positioned plateau portion 1670.

The interior surface 1660 and engagement mechanism 1626 of the tines 1614 may further include a second ramp or sloped portion 1672 extending from the plateau portion 1670 and towards the bridge 1612, as shown in FIG. 31. The second ramp portion 1672 may be substantially planar. As shown in FIG. 31, the second ramp portion 1672 may be angled inwardly towards the other tine 1614 of the staple 1610 at it extends away from the plateau portion 1670 and towards the bridge 1614. In some embodiments, the second ramp portion 1672 may be angled inwardly towards the other tine 1614 of the staple 1610 at it extends away from the plateau portion 1670 and towards the bridge 1614 at an angle less than or equal to about 10 degrees. The second ramp portion 1672 and the plateau portion 1670 may be oriented at an obtuse angle with respect to each other and the interior of the staple 1610. The second ramp portion 1672 may define a length longer than that of the first ramp portion 1668 and/or the plateau portion 1670 (e.g., a length in the vertical direction).

The interior surface 1660 and engagement mechanism 1626 of the tines 1614 may also include a first relief portion 1674 extending from the second ramp portion 1672, as shown in FIG. 31. The first relief portion 1674 may extend away from the other tine 1614 of the staple 1610 (i.e., away from the interior of the staple 1610). In this way, the first relief portion 1674 and the second ramp portion 1672 may be oriented at an acute angle with respect to each other and the interior of the staple 1610. The first relief portion 1674 may be substantially planar, arcuate, or a combination thereof. The junction of the relief portion 1674 and the second ramp portion 1672 may form a tip 1676. The tip 1676 may be positioned further inwardly toward the other tine 1614 of the staple 1610 than the plateau portion 1670. In this way, the second ramp portion 1672 and first relief portion 1674 of the interior surface 1660 and engagement mechanism 1626 of the tines 1614 may form a first interior barb structure 1675.

The first ramp portion 1668 and the plateau 1670 positioned adjacent to the first interior barb structure 1675 (e.g., the plateau 1670 and the second ramp portion 1672 of the barb structure 1675 being adjacent) may allow the engagement mechanism 1626 of the staple 1610, in situ, to exert a greater amount of compressive force and a more uniform compressive force to the biological elements or other material positioned substantially between the tines 1614 following implantation of the staple 1610. For example, the ramp portion 1668 and/or the plateau 1670 may act to increase the potential compressive load of the staple 1610, in situ, as compared to an identical staple 1610 with the first interior barb structure 1675 and not the first ramp portion 1668 and/or the plateau 1670.

As shown in FIG. 31, the interior surface 1660 and engagement mechanism 1626 of the tines 1614 may include a first depression, gullet or valley portion 1678 extending from the first relief portion 1674. The first gullet portion 1678 may be substantially planar, arcuate, or a combination thereof. The first gullet portion 1678 may extend from the first relief portion 1674 and at least towards the bridge 1612. In some embodiments, the first gullet portion 1678 may extend between the first relief portion 1674 and at least one additional interior barb structure 1675', as explained further below. The first gullet portion 1678 may be positioned further inwardly (i.e., towards the other tine 1614 of the staple 1610) than the first portion 1666 of the interior surface 1660 (e.g., at about the same position as the plateau portion 1670).

The interior surface 1660 and engagement mechanism 1626 of the tines 1614 may include at least one additional interior barb structure 1675' between the first interior barb 1675 and the bridge 1612. For example, as shown in FIG. 31, the interior surface 1660 and engagement mechanism 1626 may include a third ramp portion 1672', a second relief portion 1674, a second tip 1676' between the third ramp portion 1672' and the second relief portion 1674, and a second gullet portion 1678'. The third ramp portion 1672', second relief portion 1674, second tip 1676', and second gullet portion 1678' of the at least one additional barb 1675' may be substantially similar to the second ramp portion 1672, first relief portion 1674, first tip 1676, and first gullet portion 1678, respectively, of the first barb 1675. However, in alternative embodiments the at least one additional barb 1675' may differ from the first barb 1675 in at least one aspect. If the interior surface 1660 and engagement mechanism 1626 of the tines 1614 includes a plurality of barbs, the first ramp portion 1668 and/or the plateau 1670 may also be positioned between adjacent barbs or before each of the barbs (i.e., positioned on the tip portion 1618 side of each of the barbs).

Figure 32:
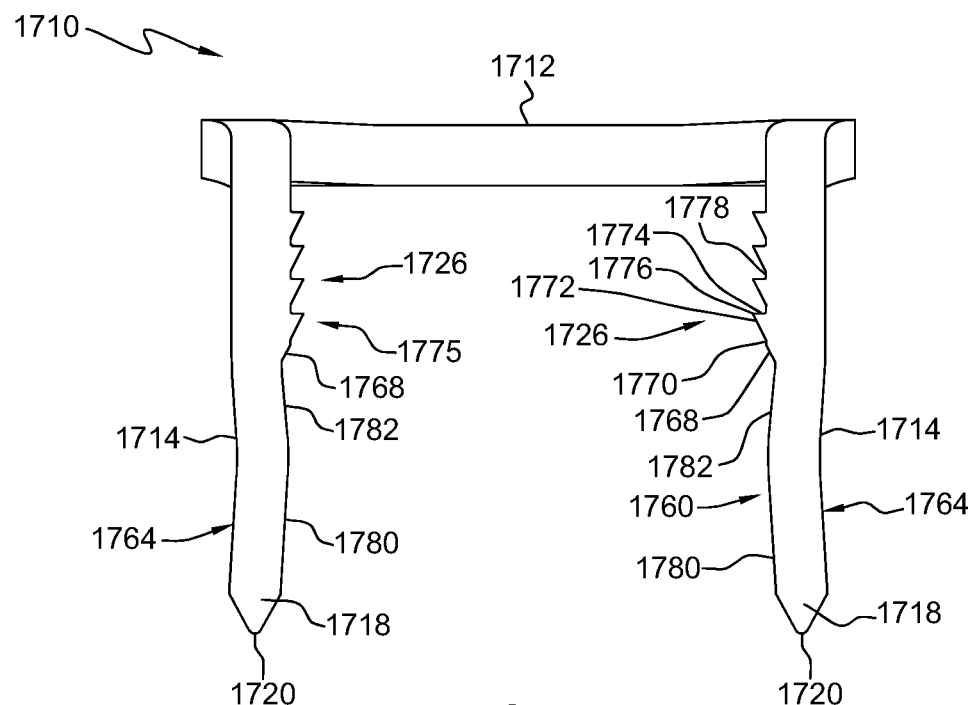
FIG. 32 illustrates a back view of another staple according to the present disclosure.
Figure 33:
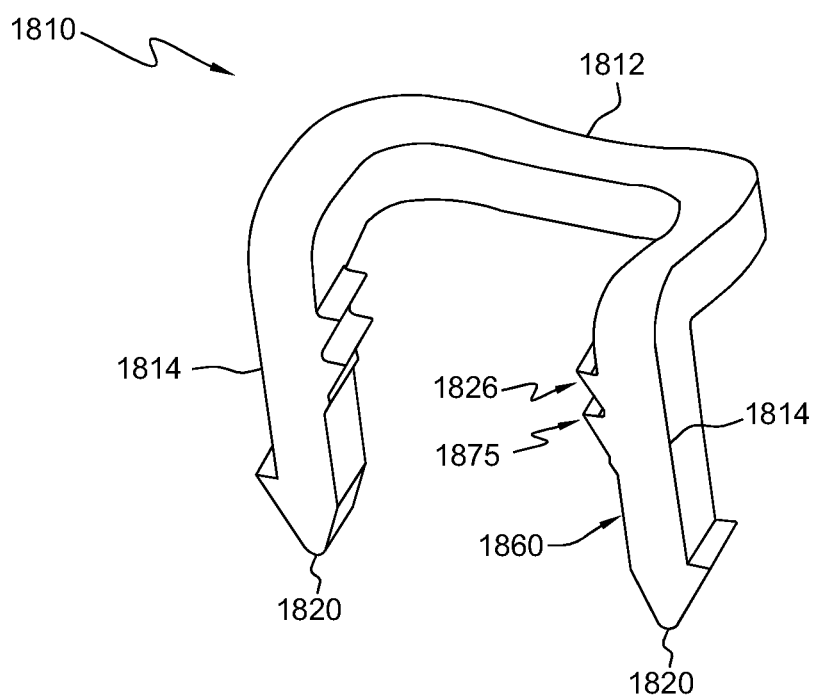
FIG. 33 illustrates a perspective view of another staple according to the present disclosure.

Similar to the staple 1610 of FIGS. 26-31, the engagement mechanism 1726 of the tines 1714 of the staple 1710 shown in FIG. 32 is configured to engage biological elements, and to increase the compressive load of the tines 1714 and/or engagement mechanisms 1726 to the biological elements as compared to tines or engagement mechanisms of other staple designs. The tines 1714 and engagement mechanisms 1726 of the staple 1710 of FIG. 32 differ from the tines 1614 and engagement mechanisms 1626 of FIGS. 26-31 in the configuration of the portion of the interior surfaces 1760 of the tines 1714 distal to the first ramp 1768 (i.e., the portion of the tines 1714 proximate to the end portions 1718 thereof). As shown in FIG. 32, the interior surfaces 1760 of each tine 1714 may include a first portion 1780 and a second portion 1782 that, in combination, extend between the end portion 1720 and the first ramp 1768 of the tines 1714. The first portion 1780 of the tines 1714 that is adjacent the tip portion 1718 may be angled (e.g., at an acute angle) inwardly toward the opposing tine 1714 of the staple 1710 at it extends from the end portion 1718 and towards the bridge 1712, as shown in FIG. 32. The second portion 1782 of the tines 1714 may extend between the first portion 1780 and the first ramp 1768. As shown in FIG. 32, the second portion 1782 may be angled (e.g., at an acute angle) outwardly away from the opposing tine 1714 of the staple 1710 at it extends from the first portion 1780 to the first ramp 1768. The first portion 1780 and second portions 1782 of the interior surfaces 1660 of the tines 1714 of the staple 1710 may each extend, approximately, about the half distance between the tip portion 1718 and the first ramp 1768.

The outer-facing sides 1764 of the tines 1714 (i.e., the surfaces facing away from the opposing tine 1714) may include portions that are planar or extend parallel to the first portion 1780 and second portion 1782 of the interior surfaces 1760 of the tines 1714, as shown in FIG. 32. In some alternative embodiments, however, the outer-facing sides 1764 of the tines 1714 may be oriented and/or shaped differently than the first portion 1780 and second portion 1782 of the interior surfaces 1760 of the tines 1714. For example, the first portion 1780 and the second portion 1782 of the interior surfaces 1760 of the tines 1714 may be angled as described above, but the outwardly-facing sides 1764 may extend substantially vertically (i.e., may not be angled), or vice-versa.

As shown in FIG. 32, the interior surface 1760 and engagement mechanisms 1726 of each tine 1714 includes a plurality of barb structures 1775. The barb structure 1775 that is proximate to the free end 1720 of the tines 1714 includes a ramp portion 1768 and a plateau portion 1770 between the tip 1776 and the second portion 1782 of the tines 1714 (as discussed above). Additional barb structures 1775 (e.g., three additional barb structures 1775) are provided proximate to the bridge portion 1712. The additional barb structures 1775 are arranged consecutively without a ramp portion 1768 and/or plateau portion 1770 therebetween. In alternative embodiments, however, at least one of the additional barb structures 1775 may include a ramp portion 1768 and/or plateau portion 1770 between the respective structure 1775 and an adjacent structure 1775.

Figure 34:
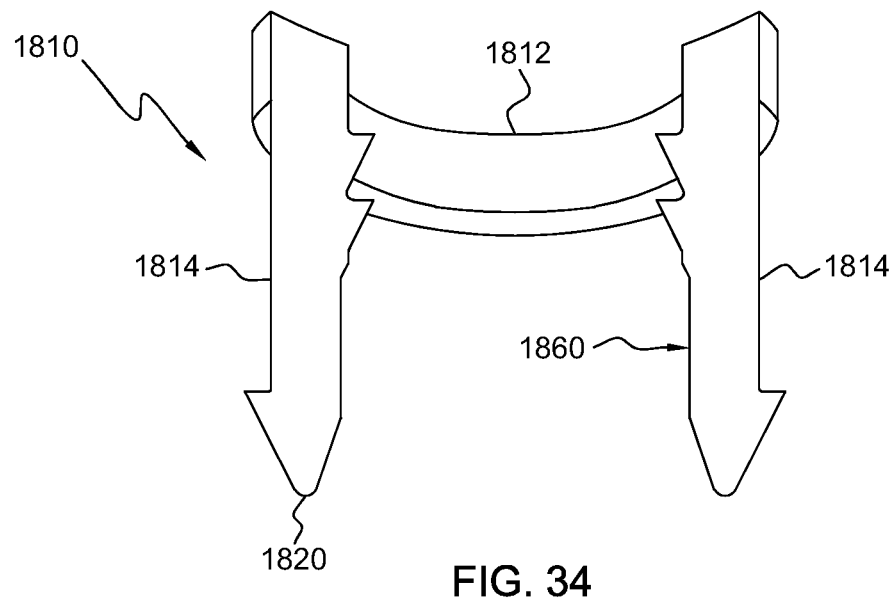
FIG. 34. illustrates a back view of the staple of FIG. 33.
Figure 35:
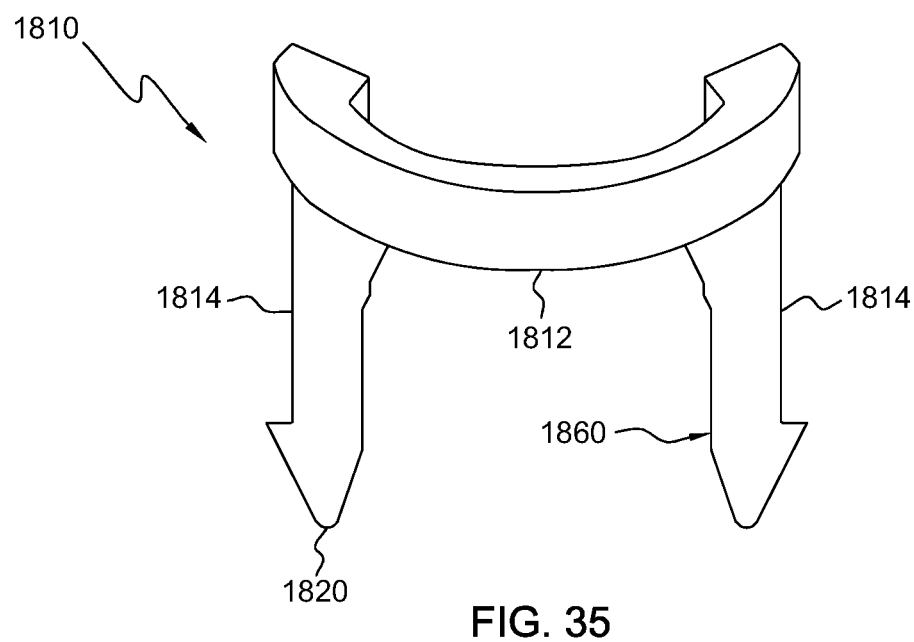
FIG. 35. illustrates a front view of the staple of FIG. 33.
Figure 36:
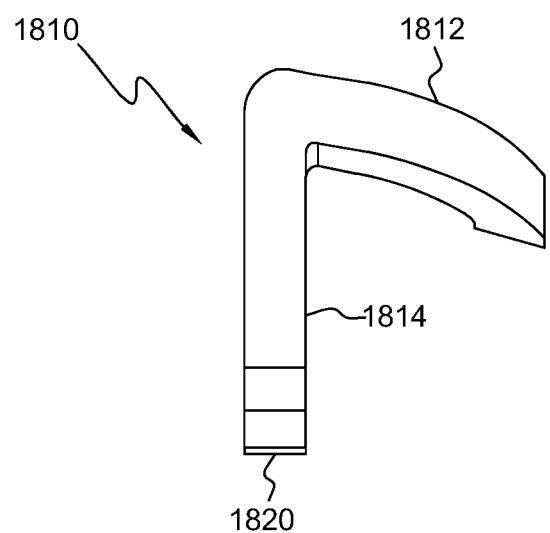
FIG. 36. illustrates a side view of the staple of FIG. 33.
Figure 37:
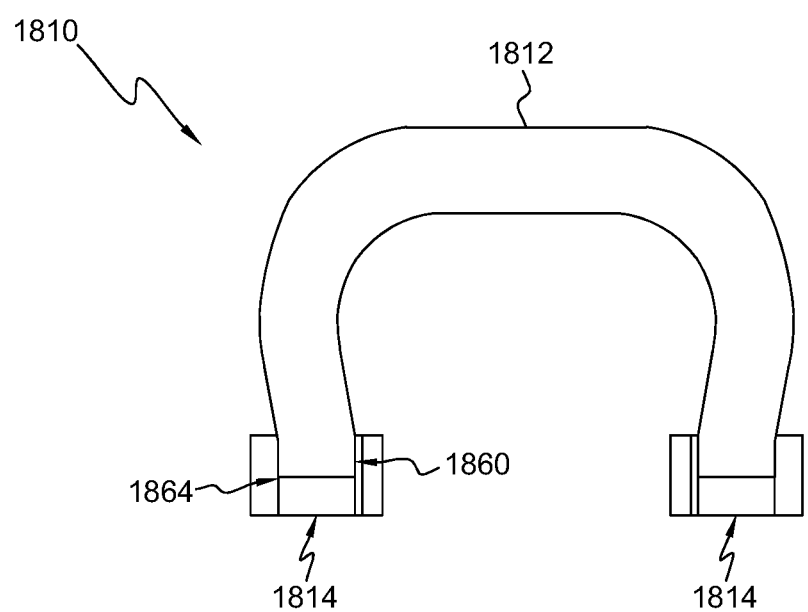
FIG. 37 illustrates a top view of the staple of FIG. 33.

FIGS. 33-37 illustrate another offset staple 1810 that includes the tine 1814 configuration described above and shown in FIGS. 26-31. However, other tine configurations may be utilized. A difference between the offset staple 1810 of FIGS. 33-37 and the offset staple 1610 of FIGS. 26-31 is the configuration of the offset bridge 1812. The bridge 1812 of FIGS. 33-37 is substantially rectangular in cross-section and forms a radiused or arcuate shape as it extends between the tines 1814. More specifically, the bridge 1812 forms a substantially horseshoe or "U" shape when viewed from above (see FIG. 37). As shown in FIG. 34, the bridge 1812 is curved or angled downward toward the free ends 1820 of the tines 1814 as it extends away from the tines 1814 on a side (i.e., angled on a side of the tines 1814). In some such embodiments, the offset bridge 1812 may be angled downwardly from the horizontal within the range of about 10 degrees to about 20 degrees (e.g., if the staple 1810 is oriented such that the tines 1814 extend substantially vertically). The offset bridge 1814 is also convex in the direction extending substantially between the tines, 1814 as shown in FIGS. 33-37. In this way, the intermediate portion of the bridge 1812 positioned between the tines 1814 may be the portion of the bridge 1812 that is positioned closest to the free ends 1820 of the tines 1814 (i.e., is the lowest portion in the vertical direction as shown in FIG. 36), and the adjacent portions of the bridge 1814 may extend therefrom to one side and vertically to the top portions of the tines 1814.

Figure 38:
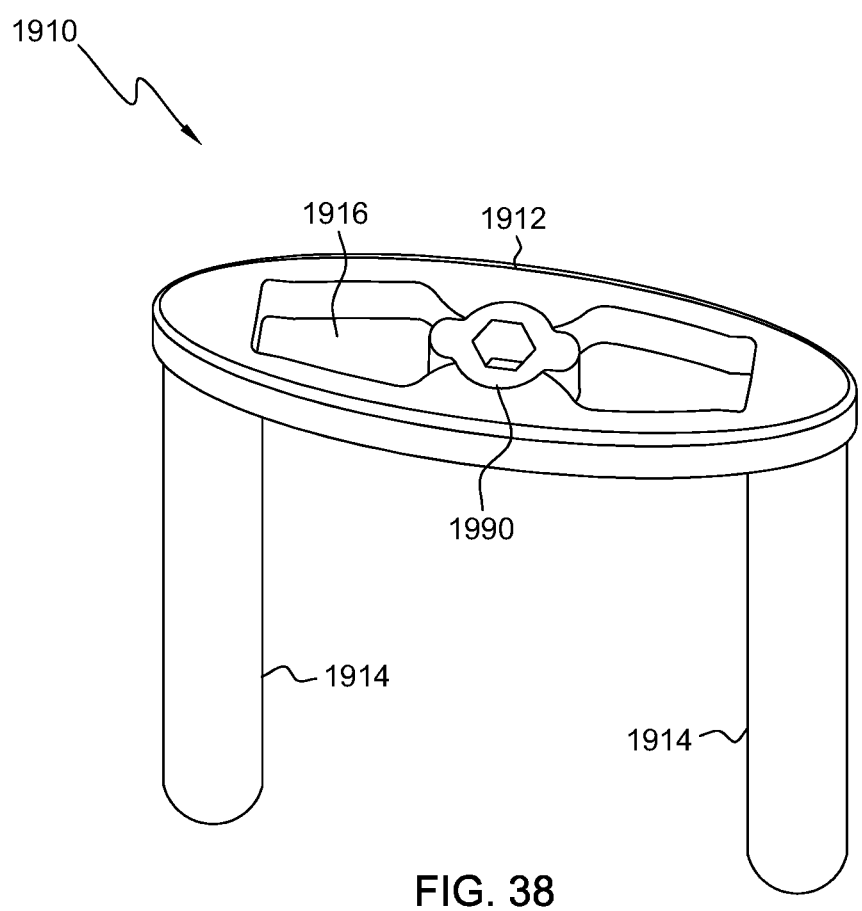
FIG. 38 illustrates a perspective view of another staple according to the present disclosure.

As shown in FIG. 38, the staple 1910 may include a secondary member or element 1990 that is operable to at least assist in elastically deforming of the offset bridge 1912 and/or maintaining the deformed or a compressed state of the offset bridge 1912. For example, as shown in FIG. 38, the offset bridge 1912 of the staple 1912 may be shaped or otherwise configured such that selective placement of the secondary element 1990 within an aperture or cavity 1916 of the offset bridge 1912 (or otherwise coupling the secondary element 1990 with the offset bridge 1912) (such as after implantation of the tines 1914 in biological elements) may deform or bias the offset bridge 1912 such that the relative spacing of the tines 1914 is shortened to thereby apply a compressive force between the tines 1914. In other embodiments, the offset bridge 1912 of the staple 1910 may be shaped or otherwise configured such that selective placement of the secondary element 1190 within an aperture 1916 of the offset bridge 1912 (or otherwise coupling the secondary element 1990 with the offset bridge 1912) (such as prior to implantation of the tines 1914 in biological elements) may elastically deform or bias the offset bridge 1912 such that the relative spacing of the tines 1914 is increased. In such embodiments, the secondary element 1190 may be selectively removed from engagement with the offset bridge 1912 (such as after implantation of the tines 1914 in biological elements) to allow the bridge 1912 to release the elastic deformation ma of the offset bridge 1912 such that the relative spacing of the tines 1914 is shortened to thereby apply a compressive force between the tines 1914. Further, as shown in FIG. 38, the offset bridge 1912 of the staple 1910 may be operable such that selective placement of the secondary element 1990 within an aperture 1916 of the offset bridge 1912 (or otherwise coupling the secondary element 1990 with the offset bridge 1912) may elastically deform or bias the offset bridge 1912 and selectively maintain or "hold" the offset bridge 1912 in such a deformed or biased state (whether in an "extended" state or a "compressed" state, as described above). In this way, selective removal or disengagement of the secondary element 1990 from the offset bridge 1912 may release the elastic deformation and allow the bridge 1912 to return to its previous state (e.g., a natural state) and thereby apply a compressive force between the tines 1914. In some embodiments, the staple 1910 may initially be provided with the secondary element 1990 maintaining the offset bridge 1912 in the deformed or biased state such that selective removal of the secondary element 1990 (such as after implantation of the tines 1914 in biological elements) releases the elastic deformation of the bridge 1912 to allow the bridge 1912 to return to its previous state (e.g., a natural state) and thereby apply a compressive force between the tines 1914. The secondary element 1990 may be made from a same material as the staple 1910, or be made of a differing material as the staple 1910.

Figure 39:
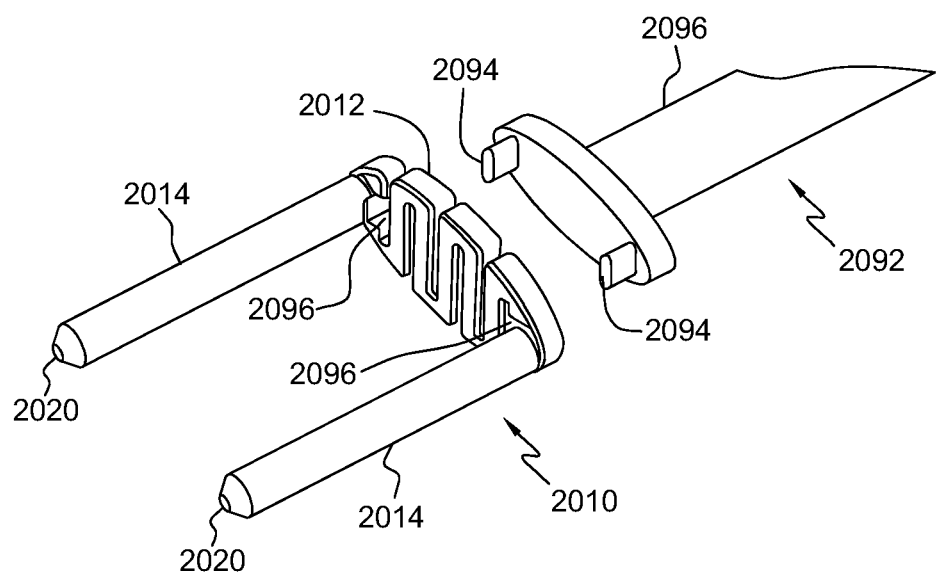
FIG. 39 illustrates a perspective view of another staple and a staple delivery guide according to the present disclosure.

As shown in FIG. 39, the present disclosure provides for a staple delivery guide 2092 that may be effective in facilitating use of the staples disclosed herein. For example, as shown in FIG. 39, a staple delivery guide 2092 may include a manually engageable handle 2096 and at least a pair of protrusions or other engagement mechanisms 2094 provided at an end portion of the handle 2096. The engagement mechanisms 2094 may be configured to mate with corresponding apertures or other engagement mechanisms 2096 of a staple 2010. The staple 2010 may include an offset bridge 2012 and the tines 2014 described herein. The engagement mechanisms 2096 of the staple 2010 may be provided within the bridge 2012 and/or the tines 2014.

The engagement mechanisms 2094 of the staple delivery guide 2092 may be operable to removably engage the corresponding engagement mechanisms 2096 of the staple 2010 and at least selectively maintain the extended or biased state of the staple 2010. In other embodiments, the staple 2010 may not include the engagement mechanisms 2096, and the engagement mechanisms 2094 of the staple delivery guide 2092 may be configured to engage portions of the staple 2010 (e.g., portions of the bridge 2012, tines 2014, etc.) and at least selectively maintain the extended or biased state of the staple 2010. The staple delivery guide 2092 may thereby be operable to maintain a deformed or biased state of the staple 2010 to effectuate implantation of the staple 2010 in the extended or biased state (i.e., implantation of the tines 2014 into biological elements). For example, the staple delivery guide 2092 may engage and maintain the extended or biased state of the staple 2010, and the free ends 2020 of the tines 2014 may be driven or otherwise forced into biological elements by via force applied through the handle 2096 of the staple delivery guide 2092.

After implantation, the engagement mechanisms 2094 of the staple delivery guide 2092 may be selectively disengaged from the corresponding engagement mechanisms 2096 of the staple 2010. For example, the staple delivery guide 2092 and or the staple 2010 may be configured such that relative force above a defined threshold between the engagement mechanisms 2094 of the staple delivery guide 2092 and the staple 2010 may disengage the engagement mechanisms 2094 from the staple 2010. For example, after implantation of the staple 2010, the staple delivery guide 2092 may be forced away from the biological elements and the staple 2010 in a direction substantially opposing an implantation direction (e.g., along an implantation direction defined by the orientation and configuration of the tines 2014) which forces the engagement mechanisms 2094 to disengage from the implanted staple 2010. In some embodiments, after implantation of the staple 2010, the staple delivery guide 2092 may be forced in a direction angled with respect to the implantation direction.

In some embodiments, the staple delivery guide 2092 may also be operable to deform or bias the offset bridge 2012 into the extended or biased state. In some embodiments, the staple 2010 may be provided engaged with the delivery guide 2092 in the extended or biased state to a user. For example, a staple kit may contain one or more delivery guides 2092 with staples 2010 removably engaged thereto in the extended or biased state.

Figure 40:
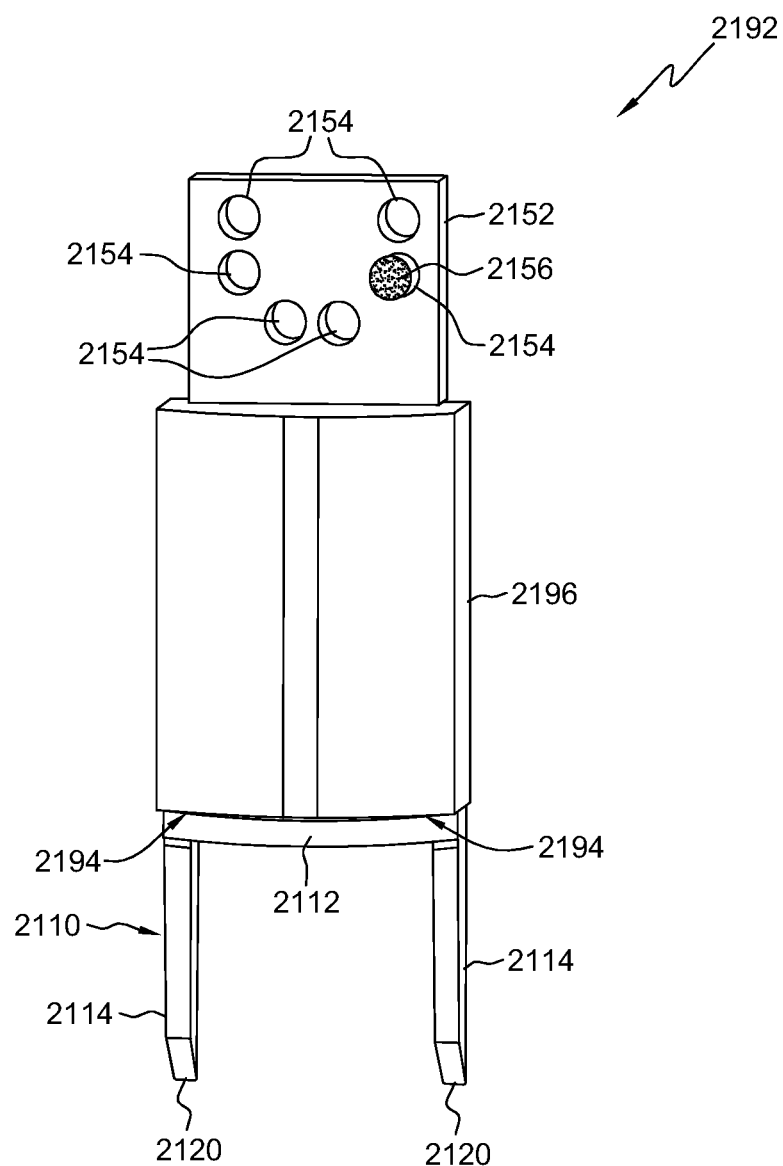
FIG. 40 illustrates an elevational perspective view of a staple delivery and drill guide according to the present disclosure.

As shown in FIG. 40, the present disclosure further provides for a staple delivery and drill guide 2192. The staple delivery and drill guide 2192 may include a staple engagement portion 2194 provided at one portion of a handle portion 2196 that is configured to removably engage or couple with an offset staple, such as those described above. The engagement portion 2194 of the staple delivery and drill guide 2192 may be operable to removably engage a staple 2110 and at least selectively maintain the extended or biased state of the staple 2110, as shown in FIG. 40 and described above. In some embodiments, the engagement portion 2194 of the staple delivery guide 2192 may also be operable to elastically deform or bias the offset bridge 2112 of the staple 2110 from the neutral state to the extended or biased state, as described above. For example, the staple engagement portion 2194 of the staple delivery and drill guide 2192 may include rails that engage and/or otherwise move or translate the tines 2114 from the neutral position to the extend position—thereby deforming or biasing the bridge 2112. In this way, the bridge 2112 may be pre-loaded in tension such that the bridge 2112 applies a pre-loaded compression force to the tines 2114 in the extended position of the tines 2114 (i.e., the extended state of the staple 2110). In alternative embodiments, the staple engagement portion 2194 may engage the bridge portion 2112 and be operable to move bias the bridge member 2112 into the extended state to move the tines 2114 into the extended position. In some embodiments, the staple engagement portion 2194 may also maintain the deformed or biased state of the offset bridge 2112 to maintain the extended position of the tines 2114 and thereby facilitate insertion of the staple 2110 in biological elements in the pre-loaded deformed or biased state, as described below.

On another portion of the handle portion 2196, the staple delivery and drill guide 2192 may include a drill guide portion 2152, as shown in FIG. 40. The drill guide portion 2152 may be configured to facilitate the formation of apertures in biological elements with a drill bit or other mechanism, as shown in FIG. 40. The apertures formed in the biological elements via the drill guide portion 2152 may facilitate the insertion of the tines 2114 of the staple 2110 in the biological elements.

As shown in FIG. 40, the drill guide portion 2152 of the offset staple guide 2192 may include openings 2154. The openings 2154 may include a plurality of pairs of openings 2154 to facilitate the formation of the apertures in the biological elements at differing spacing to accommodate differing offset staple 2110 designs or sizes and/or differing biological elements or biological conditions, as shown in FIG. 40. The openings 2154 of the drill guide portion 2152 may be spaced such that that a corresponding offset staple 2110 must be elastically deformed or biased into the extended state for the tines 2114 to be aligned with (and ultimately insert into) the apertures formed in biological elements via the openings 2154. Stated differently, the pair(s) of openings 2154 of the drill guide portion 2152 may be spaced further apart than the tines 2114 of a corresponding offset staple 2110 in a neutral position or state of the offset staple 2110. In this way, the offset bridge 2112 must be elastically deformed or biased into the extended or biased state to align and insert the tines 2114 into the apertures formed in biological elements via the openings 2154.

As also shown in FIG. 40, the openings 2154 of the drill guide portion 2152 may also allow a securing member 2156 to extend through the drill guide portion 2152 and into the biological elements to temporality secure the guide 2192 to the biological elements. Coupling or securing the guide 2192 to one or more biological elements via the openings 2154 and at least one securing member 2156 may provide for accurate formation of apertures in the biological elements and across a junction between the biological elements. After formation of the apertures in the biological elements via the drill guide portion 2152, the guide 2192 may be removed from the biological elements via removal of the at least one securing member 2156 and utilized to insert the tines 2114 of a corresponding staple 2110, in the extended or biased state, into the apertures to attach the staple 2110 to the biological elements. After insertion of the tines 2114 into the apertures in the biological elements (formed via the drill guide portion 2152), the guide 2192 can be removed or otherwise decoupled from the staple 2110. In this way, the staple delivery and drill guide 2192 are separate and distinct components, and the guide 2192 may be reused with new staples 2110 (including staples 2110 of differing sizes).

Another exemplary offset staple delivery and drill guide 2292 according to the present disclosure is shown in FIGS.

Figure 41:
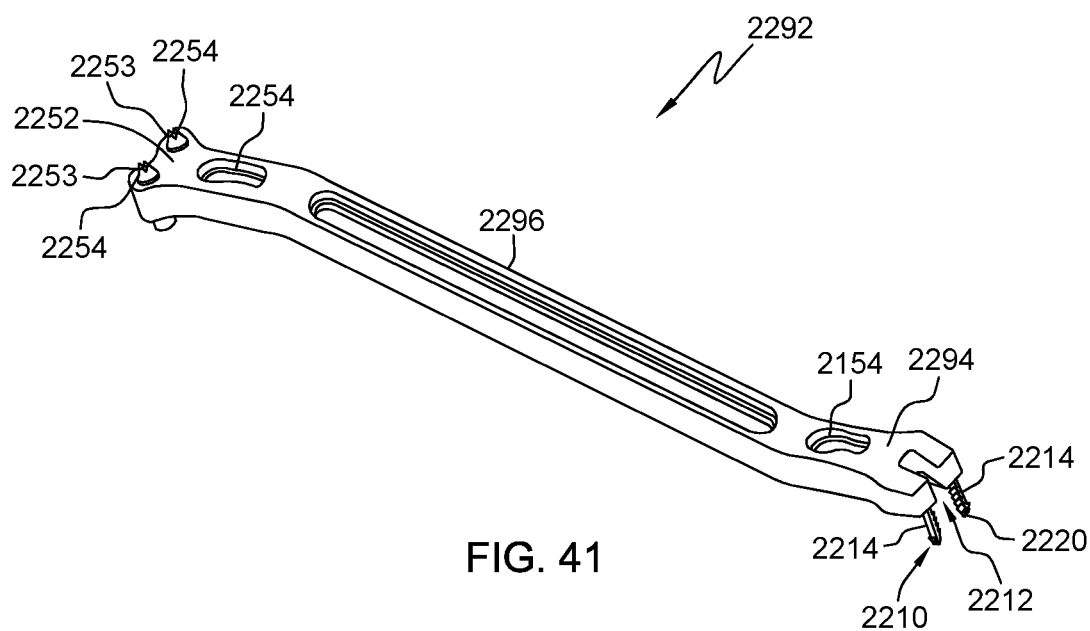
FIG. 41 illustrates a perspective view of a top portion of another staple delivery and drill guide according to the present disclosure.
Figure 42:
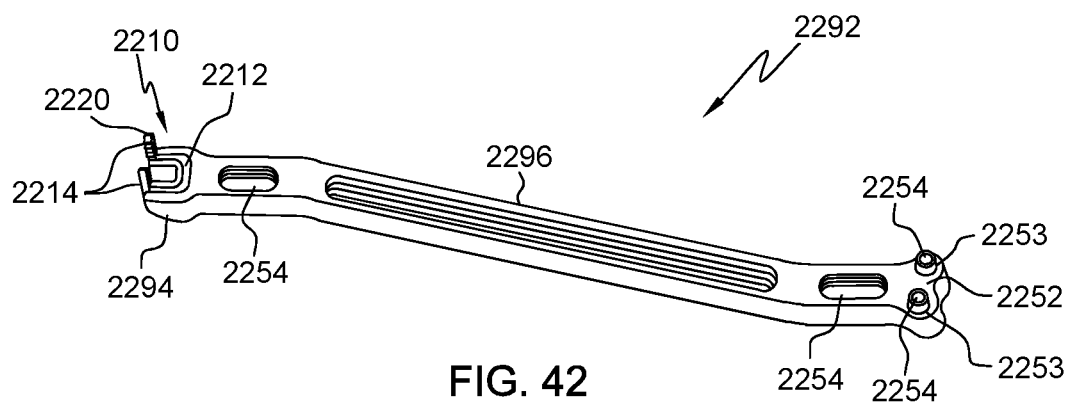
FIG. 42 illustrates a perspective view of a bottom portion of the staple delivery and drill guide of FIG. 41.

41-43. As shown in FIGS. 41 and 42, the staple delivery and drill guide 2292 may include a drill guide portion 2252 at one end of the guide 2292, a staple engagement portion 2294 at another end of the guide 2292, and a handle portion 2296 extending between the drill guide portion 2252 and the staple engagement portion 2194. The handle portion 2296 of the guide may space the drill guide portion 2252 and the staple engagement portion horizontally and/or vertically with respect to each other, as shown in FIGS. 41 and 42. The drill guide portion 2252 and the staple engagement portion 2294 may "face" opposing vertical directions such that the guide 2292 may need to be inverted or turned over vertically to utilize the drill guide portion 2252 and the staple engagement portion 2194 with respect to each other.

Figure 43:
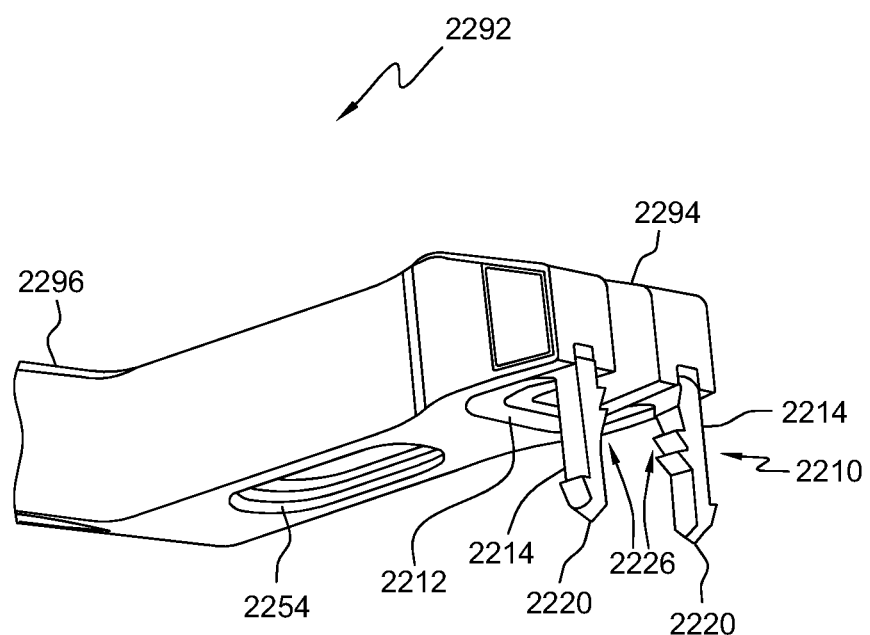
FIG. 43 illustrates an enlarged perspective view of a staple engagement portion of the staple delivery and drill guide of FIG. 41.

The staple engagement portion 2294 of the guide 2292 is configured to removably couple with an offset staple 2210, such as the offset staples described herein. The staple engagement portion 2294 may be configured with a groove, channel or other engagement mechanism configured to removably engage or "hold" an offset staple 2210 in the elastically deformed or biased state of the staple 2210 as shown in FIGS. 42 and 43—e.g., an elastically deformed or biased state of the offset bridge 2212 of the staple 2210. An offset staple 2210 may be pre-loaded in the staple engagement portion 2294 before use of the guide 2292, or a user may manually engage an offset staple 2210 with the staple engagement portion 2294 before use. As shown in FIGS. 41-43, the staple engagement portion 2294 of the guide 2292 may be configured to removably engage an offset staple 2210 (e.g., the bridge portion 2212 thereof) such that the tines 2214 of the staple 2210 extend freely from the guide 2292. In this way, the staple engagement portion 2294 of the guide 2292 may facilitate insertion of the tines 2214 of the offset staple 2210 into biological elements in the pre-loaded deformed or biased state of the staple 2210 (i.e., the bridge 2212 applying a pre-loaded compression force to the tines 2214). After insertion of the tines 2214 of the offset staple 2210 into biological elements, the staple engagement portion 2294 of the guide 2292 may be decoupled or detached from the offset staple 2210 to release or activate the pre-loaded compression force and allow the tines 2214 to act against (i.e., compress) the biological elements.

As discussed above, the guide 2292 may also include a drill guide portion 2252 configured to facilitate the formation of apertures in biological elements. The apertures formed via the drill guide portion 2252 may facilitate the insertion of the pair of tines 2214 of the staple 2210 engaged with the staple engagement portion 2294 of the guide 2292 into the biological elements, as described above. The drill guide portion 2252 of the guide 2292 may include at least one pair of openings 2254 to facilitate the formation of the apertures with a drill or other tool, as shown in FIGS. 41 and 42. As shown in FIG. 41, one end or side of the drill guide portion 2252 (e.g., a side that opposes the side of the staple engagement portion 2294 that engages a staple 2210) may include spikes, teeth or other relatively sharp segment engagement projections or sleeves 2253 that form the openings 2254 and are configured to temporarily secure the drill guide portion 2252 to the biological elements, such as during use of the openings 2254 of the to form the apertures.

The openings 2254 and engagement sleeves 2253 of the of the drill guide portion 2252 may be spaced such that the tines 2214 of a corresponding offset staple 2210 coupled to the staple engagement portion 2294 (in the elastically deformed or biased state of the staple 2210 and/or bridge 2212) are aligned with (and ultimately insert into) apertures formed via the drill guide openings 2254 and engagement sleeves 2253. In this way, the offset staple delivery and drill guide 2292 of FIGS. 41-43 may be used both to form apertures in biological elements and to implant the tines 2214 of an offset staple 2210 engaged to the staple engagement portion 2294 in the elastically deformed or biased state (i.e., a pre-loaded state) into the apertures such that, after implantation and disengagement of the staple engagement portion 2294 from the offset staple 2210, the offset staple 2210 applies a compressive force to the biological elements via the tines 2214 (e.g., to close a space between the biological elements (if provided) and to apply a compressive force to the closed junction between the elements).

In some embodiments, the staples and guides disclosed herein may include one or be formed of a physiologically compatible material, such as a physiologically compatible metal (e.g., titanium, titanium alloy, stainless steel, nickel titanium (nitinol)), a carbon fiber, a polymer, and combinations thereof. In some embodiments, the staples and guides of the present disclosure may include one or more component or portion that is radiolucent.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably" in conjunction with terms such as coupled, connected, joined, sealed or the like is used herein to refer to both connections resulting from separate, distinct components being directly or indirectly coupled and components being integrally formed (i.e., one-piece, integral or monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims. Further, any aspect, component, function, other feature disclosed herein with respect to a particular staple or guide embodiment may equally be employed with a differing staple or guide embodiment disclosed herein for its same or similar purpose.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A staple for applying a compressive force between biological elements, comprising:
    a non-linearly extending bridge portion;
    the bridge portion connecting a pair of tines and forming a U-shape between the pair of tines, the bridge portion bounding an open space between the pair of tines;
    the pair of tines extending from the bridge portion and including free ends configured to be implanted into the biological elements, the pair of tines being spaced apart a first distance in a first state of the bridge portion;
    wherein the bridge portion is elastically deformable into a second state such the pair of tines are spaced apart a second distance that is greater than the first distance;
    wherein each tine of the tines extends along a first direction defined between the bridge portion and the free end thereof, each of the tines include an engagement mechanism positioned on a portion of the tines that substantially faces the other tine of the pair of tines along the first direction;
    wherein each engagement mechanism of the pair of tines includes:
        a first portion proximate to the free end of one of the respective tines and extending toward the bridge portion;
        a first ramp portion extending from the first portion toward the bridge portion and along the first direction toward the other tine of the pair of tines;
        a plateau portion extending from the first ramp portion toward the bridge portion;
        a second ramp portion extending from the plateau portion toward the bridge portion and along the first direction toward the other tine of the pair of tines a distance greater than the first ramp portion extends along the first direction; and
        a relief portion extending from the plateau portion and at least along the first direction away from the other tine of the pair of tine, the intersection of the relief portion and the second ramp portion forming a tip.

2. The staple of claim 1, wherein the pair of tines extend from opposing ends of the bridge portion.

3. The staple of claim 1, wherein bridge portion comprises a substantially rectangular cross-section.

4. The staple of claim 3, wherein the bridge portion connects to the pair of tines at tine connection points and extends downwardly between the tine connection points in a direction away from the tine connection points and closer to the free ends than the connection points are to the free ends.

5. The staple of claim 1, wherein the bridge portion extends between the pair of tines on a first side of the pair of tines.

6. The staple of claim 5, wherein an intermediate portion of the bridge portion is positioned furthest from of the pair of tines on the first side.

7. The staple of claim 1, wherein the engagement mechanism of the pair of tines include at least one barb structure.

8. The staple of claim 1, wherein the second ramp portion and the relief portion form a barb structure.

9. The staple of claim 1, wherein each engagement mechanism of the pair of tines further includes a plurality of the barb structures.

10. The staple of claim 1, wherein the first portion of the engagement mechanism includes a first portion proximate to the free end of the respect tine that extends toward the bridge portion and along the first direction toward the other tine of the pair of tines, and a second portion that extends from the first portion to the first ramp portion and along the first direction away from the other tine of the pair of tines.

* * * * *